United States Patent
Patzel et al.

(10) Patent No.: US 12,091,669 B2
(45) Date of Patent: Sep. 17, 2024

(54) METHOD FOR THE GENERATION OF DUMBBELL-SHAPED DNA VECTORS

(71) Applicant: NATIONAL UNIVERSITY OF SINGAPORE, Singapore (SG)

(72) Inventors: Volker Patzel, Singapore (SG); Samantha Leeanne Cyrill, New York, NY (US)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 17/637,432

(22) PCT Filed: Aug. 21, 2020

(86) PCT No.: PCT/SG2020/050488
§ 371 (c)(1),
(2) Date: Feb. 22, 2022

(87) PCT Pub. No.: WO2021/034275
PCT Pub. Date: Feb. 25, 2021

(65) Prior Publication Data
US 2022/0275378 A1    Sep. 1, 2022

(30) Foreign Application Priority Data
Aug. 22, 2019  (SG) .............. 10201907789T

(51) Int. Cl.
C12P 19/34     (2006.01)
C12N 15/64     (2006.01)
C12N 15/85     (2006.01)

(52) U.S. Cl.
CPC ............. *C12N 15/64* (2013.01); *C12N 15/85* (2013.01)

(58) Field of Classification Search
CPC ....................................................... C12Q 1/686
See application file for complete search history.

(56) References Cited

U.S. PATENT DOCUMENTS

| 6,451,563 | B1 | 9/2002 | Wittig et al. |
| 2008/0153763 | A1 | 6/2008 | Takagi et al. |

(Continued)

FOREIGN PATENT DOCUMENTS

| WO | 2012/032114 A1 | 3/2012 |
| WO | 2016/195598 A1 | 12/2016 |

OTHER PUBLICATIONS

Samantha Leeanne Cyrill: "The Design, Generation, and Investigation of Dumbbell-Shaped Minimal DNA Vectors for Delivery of Coding and Non-Coding RNA", Aug. 19, 2016, National University of Singapore.

(Continued)

*Primary Examiner* — Kenneth R Horlick
(74) *Attorney, Agent, or Firm* — Maschoff Brennan

(57) ABSTRACT

Dumbbell-shaped DNA minimal vectors represent genetic vectors solely composed of the gene expression cassette of interest and terminal closing loop structures. Dumbbell vectors for small hairpin RNA or microRNA expression are extremely small-sized which is advantageous with regard to cellular delivery and nuclear diffusion. Conventional strategies for the generation of small RNA-expressing dumbbell vectors require cloning of a respective plasmid vector which is subsequently used for dumbbell protection. Here, we present a novel cloning-free method for the generation of small RNA-expressing dumbbell vectors which also does not require any restriction endonucleases. The method comprises the PCR amplification of a universal DNA template using primers containing the sense or antisense strand of the sequence of interest, the denaturing and refolding of the amplified product to form stem-loop structures, and the structures are covalently closed using DNA ligases to obtain dumbbell structures.

11 Claims, 16 Drawing Sheets

Figure 1:
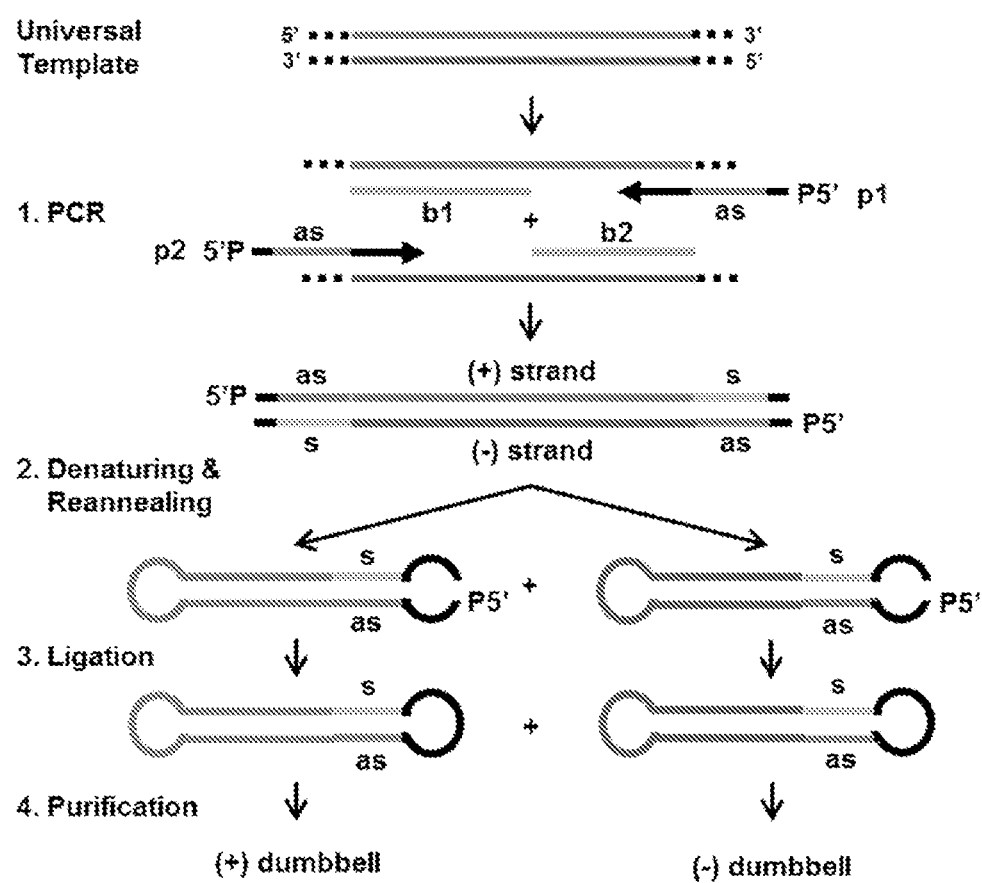

Specification includes a Sequence Listing.

(56) References Cited

U.S. PATENT DOCUMENTS

2018/0171354 A1* 6/2018 Patzel ............... C12P 19/34
2018/0265915 A1 9/2018 McArthur et al.

OTHER PUBLICATIONS

Yu H. et al., "Efficient production of superior dumbbell-shaped DNA minimal vectors for small hairpin RNA expression" Nucleic Acids Res, Jun. 11, 2015, vol. 43, No. 18, pp. e120: 1-10.
Cyrill S.L. et al., "Universal Template-Assisted, Cloning-free Method for the Generation of Small RNA-Expressing Dumbbell-Shaped DNA Vectors" Mol Ther Methods Clin Dev, Aug. 31, 2019, vol. 15, pp. 149-156.
Biasco, L., Baricordi, C. and Aiuti, A. (Apr. 20, 2012). Retroviral Integrations in Gene Therapy Trials. Mol. Ther. 20, 709-716.
Yin, H., Kanasty, R.L., Eltoukhy, A.A., Vegas, A.J., Dorkin, J.R. and Anderson, D.G. (Jul. 15, 2014). Non-viral vectors for gene-based therapy. Nat. Rev. Genet. 15, 541-555.
Mok, P.L., Cheong, S.K., Leong, C.F., Chua, K.H. and Ainoon, O. (Mar. 2012). Extended and stable gene expression via nucleofection of MIDGE construct into adult human marrow mesenchymal stromal cells. Cytotechnology. 64, 203-216.
Kaur, T., Slavcev, R.A. and Wettig, S.D. (Dec. 9, 2009). Addressing the Challenge: Current and Future Directions in Ovarian Cancer Therapy. Curr. Gene Ther. 9, 434-458.
López-Fuertes, L., Pérez-Jiménez, E., Vila-Coro, A.J., Sack, F., Moreno, S., Konig, S.A., et al. (Dec. 13, 2002). DNA vaccination with linear minimalistic (MIDGE) vectors confers protection against Leishmania major infection in mice. Vaccine. 21, 247-257.
Schakowski, F., Gorschlüter, M., Junghans, C., Schroff, M., Buttgereit, P., Ziske, C., et al. (May 2001). A Novel Minimal-Size Vector (MIDGE) Improves Transgene Expression in Colon Carcinoma Cells and Avoids Transfection of Undesired DNA. Mol. Ther. 3, 793-800.
Zanta, M.A., Belguise-Valladier, P. and Behr, J.-P. (Jan. 5, 1999). Gene delivery: A single nuclear localization signal peptide is sufficient to carry DNA to the cell nucleus. Proc. Natl. Acad. Sci. USA 96, 91-96.
8. Fogg, J.M., Kolmakova, N., Rees, I., Magonov, S., Hansma, H., Perona, J.J. et al. (Apr. 12, 2006). Exploring writhe in supercoiled minicircle DNA. J Phys Condens Matter 18: S145-S159.
9. Jiang, X., Yu, H., Teo, C.R., Tan, G., Goh, S.C., Patel, P., et al. (Sep. 24, 2016). Advanced design of dumbbell-shaped genetic minimal vectors improves non-coding and coding RNA expression. Mol. Ther. 24(9), 1581-1591.
Cost, G.J. (Sep. 6, 2007). Enzymatic ligation assisted by nucleases: simultaneous ligation and digestion promote the ordered assembly of DNA. Nat. Protoc. 2, 2198-2202.
Taki, M., Kato, Y., Miyagishi, M., Takagi, Y. and Taira, K. (Jun. 9, 2004). Small-Interfering-RNA Expression in Cells Based on an Efficiently Constructed Dumbbell-Shaped DNA. Angew. Chem., Int. Ed. 43, 3160-3163.
Taki, M., Kato, Y., Miyagishi, M., Takagi, Y., Sano, M. and Taira, K. (Sep. 1, 2003). A Direct and efficient synthesis method for dumbell-shaped linear DNA using PCR in vitro. Nucleic Acids Symp. Ser. 3, 191-192.
Jiang, X. and Patzel, V. (Jun. 5, 2017). Formation of Minimised Hairpin Template-transcribing Dumbbell Vectors for Small RNA Expression. Bio-Protocol. 7(11), 1-10.
Myslinski, E., Ame, J.C., Krol, A. and Carbon, P. (Jun. 15, 2001). An unusually compact external promoter for RNA polymerase III transcription of the human H1RNA gene. Nucleic Acids Res. 29, 2502-2509.
Zeng, Y., Wagner, E.J. and Cullen, B.R. (Jun. 9, 2002). Both natural and designed micro RNAs can inhibit the expression of cognate mRNAs when expressed in human cells. Mol. Cell. 9, 1327-1333.
Zuker, M. (Jul. 2003). Mfold web server for nucleic acid folding and hybridization prediction. Nucleic Acids Res. 31, 3406-3415.
Hofacker, I.L. (Jul. 1, 2003). Vienna RNA secondary structure server. Nucleic Acids Res. 13, 3429-3431.

* cited by examiner

METHOD FOR THE GENERATION OF DUMBBELL-SHAPED DNA VECTORS

FIELD OF THE INVENTION

The disclosure relates to a novel universal template-assisted cloning-free method allowing the efficient synthesis of dumbbell-shaped DNA vectors at low cost for delivery of recombinant DNA and RNA into host cells.

The sequence listing disclosed herein is included in a text file having the name "D3074-10011US01-Sequence_Listing," created on Aug. 10, 2023, having a size of 12,288 bytes. The foregoing text file is incorporated herein by reference.

BACKGROUND OF THE INVENTION

The efficiency of methods such as gene therapy of inherited and acquired genetic diseases, genetic vaccination, stem cell programming, somatic cell reprogramming, immunotherapy, CRISPR/Cas-mediated genome editing and manipulation of protein expression in vivo is dependent on the delivery of recombinant DNA into primary cells ex vivo or in vivo in order to trigger the expression of non-coding RNAs or proteins.

In primary cells, the expression of recombinant foreign episomal DNA (such as plasmids) is silenced within 24 hours post-delivery independent of the route of delivery. The mechanisms underlying this effect are poorly understood. Only integrating viral delivery vectors, such as retroviral, lentiviral, and AAV vectors have been successfully used to trigger medium and long-term expression in primary cells. These vectors, however, are costly considering current good Manufacturing Practise (cGMP) production standards. It is considered to be several orders of magnitude more expensive to produce viral vectors under cGMP standards than generating an equivalent quantity of 'naked' genetic material. In addition, viral vectors harbour safety risks and concerns which are associated (i) with negative interference of the integrated foreign DNA at the loci of integration (e.g. disruption of gene function and regulation), and (ii) with the involvement of components originating from pathogenic viruses.

Alternatively, the direct delivery of functional RNA into primary cells results in rapid degradation and providing only short-term effects. Hence, there is a strong desire for the development of novel genetic vectors that escape transgene silencing.

Novel vectors such as DNA minicircles or dumbbell-shaped vectors consisting solely of a transcription unit comprising promoter, coding genes and RNA-stabilising sequences, have several advantages such as improved cellular delivery or nuclear diffusion due to the small size. Moreover, these small vectors are resistant to exonucleases due to the covalently closed structure, whereas plasmids often harbour single-strand breaks, so-called nicks, triggered by shearing forces. The lack of unnecessary bacterial sequences or resistance proteins eliminates unwanted side effects in the host, and the controlled in vitro synthesis and the option to chemically link fluorophores, cell-penetrating peptides, antibodies, aptamers, sugars or immune stimulatory peptides to the loop structures, allows easy manipulation of these vectors.

As described above transgenic silencing in plasmids is frequent. DNA minicircles lacking extragenic spacers between the 5' and 3' ends of the transgene expression cassette were shown to allow sustained transgene expression in mice. When compared with minicircles, dumbbell-shaped vectors can be an order of magnitude smaller in molecular weight, in particular those for the expression of small non-coding RNA. WO2012/032114 discloses a DNA expression construct comprising a dumbbell-shaped circular vector which maintains expression for seven days post injection into melanomas. The synthesis of dumbbell shaped vectors when compared to the production of traditional vectors is often complex and costly. State-of-the-art techniques are typically enzyme dependent and additionally requiring cloning and chemical synthesis. Although improvements in the methodology have been made, such as disclosed in US2008/0153763 utilising a PCR-based techniques for the synthesis of dumbbell vectors, the methods are still largely dependent on cloning and restriction enzymes making the production of dumbbell shaped vectors costly.

MicroRNAs (miRNA) represent small non-coding RNAs (ncRNA) that post-transcriptionally regulate gene expression in most metazoans. They are transcribed from miRNA genes as primary miRNA transcripts (pri-miRNA), which are being processed to hairpin-structured precursor miRNA (pre-miRNA) in the nuclei prior to being exported into the cytoplasm where they are further processed to form short imperfectly paired RNA duplexes (miRNA:miRNA). Small or short hairpin RNAs (shRNA) are artificial hairpin-structured RNAs that mimic pre-miRNA and that can endogenously be transcribed from recombinant genes to efficiently trigger RNA interference (RNAi). For non-coding RNA, including pre-miRNA, and shRNA, and coding RNA gene delivery, researchers explore viral or non-viral delivery vectors. While viral vectors are costly and often trigger immune responses or pose the risk of genomic vector integration, many non-viral delivery vectors involve non-nucleic acid helper functions that can be toxic to the cells.[1,2] The simplest non-viral vectors are naked DNA-based vectors systems, three different types of which have been described so far: plasmids, DNA minicircles, and dumbbell-shaped DNA minimal vectors. Whereas plasmid-based gene expression is rapidly silenced in primary cells and in vivo, minicircles and dumbbell vectors do not suffer from transgene silencing and have shown promising results in pre-clinical and clinical trials.[3-7] However, compared to minicircles which require a minimum size of 300 base pairs (bp) due to circular tension,[8] dumbbell vectors have no lower size limit and can virtually be as short as the shRNA gene. The small dumbbell size, in combination with its linear structure, was shown to facilitate cellular delivery and, in particular, nuclear vector diffusion.[9]

Four methods have been reported for the generation of shRNA expressing dumbbell vectors: Firstly, enzymatic ligation assisted by nucleases (ELAN), a protocol in which intermolecular dumbbell ligation is supported by endonucleolytic cleavage of misligated off-pathway products;[10] secondly, a protocol in which the expression cassette is amplified by PCR followed by nicking enzyme cleavage to produce 5' overhangs which then form the dumbbell loops in an intramolecular ligation;[11,12] thirdly, a method that combines features of the first two protocols generating size-minimised hairpin template-transcribing shRNA-expressing dumbbell vectors;[9,13] and finally, a gap-primer PCR-based method which employs chemically modified primers and an intramolecular ligation for the efficient generation of superior dumbbell vectors that are characterised by internal loops and improved nuclear targeting activities.[14] In general, protocols forming the dumbbell structure during an intramolecular ligation reaction exhibit highest vector yields. In order to generate dumbbell vectors for the expression of novel non-coding or coding RNAs, all of the above protocols depend on a cloning step and/or require endonucleases.

The disclosed method allows for the cloning-free generation of hairpin template-transcribing dumbbell-shaped vectors for non-coding RNA, including pre-miRNA and shRNA RNA, and coding RNA expression. It describes a PCR-based method that uses a universal template whereby sequences coding for a specific pre-miRNA, shRNA, protein or peptide are introduced by the PCR primers. This novel protocol produces size-minimised hairpin-template transcribing dumbbells, does not require any restriction or nicking endonucleases, and is high throughput compatible. The disclosed method expedites and cheapens the generation of pre-miRNA, shRNA, and coding RNA expressing dumbbell vectors. The disclosed method allows highly parallelised dumbbell vectors production as required for functional genomics and screening studies and it allows large-scale dumbbell production as required for preclinical and clinical applications.

Statements of Invention

According to an aspect of the invention there is provided a dumbbell-shaped expression vector wherein said vector comprises:
i) one or more linear or hairpin-shaped transcription cassettes each comprising a nucleotide sequence encoding a nucleic acid molecule to be expressed;
ii) operably linked to said transcription cassette a minimal transcription promoter nucleotide sequence;
iii) a nucleotide sequence comprising a DNA nuclear targeting sequence;
iv) a nucleotide sequence comprising an enhancer nucleotide sequence and optionally at least one intron associated with said enhancer nucleotide sequence to enhance expression of said expressed nucleic acid molecule;
v) a nucleotide sequence comprising a post-transcriptional regulatory element or a constitutive nuclear transport element; and
vi) a nucleotide sequence comprising a sequence with homology to a part of a mammalian genome that can serve as repair template which is either single or double stranded for RNA-guided genome editing.

In a preferred embodiment of the invention said minimal transcription promoter sequence further comprises a transcription termination nucleotide sequence wherein transcription initiation and termination nucleotide sequences are operatively coupled.

In a further preferred embodiment of the invention said vector comprises at least one internal loop domain. Preferably, said loop domain comprises an abasic site or nucleotide mismatch.

In a preferred embodiment of the invention said abasic site comprises one or more In a preferred embodiment of the invention said abasic site comprises one or more apurinic/apyrimidinic abasic sites.

In a preferred embodiment of the invention said nucleotide mismatch comprises a tetrahydrofuran-based mimic of an abasic site.

In a preferred embodiment of the invention said post-transcriptional regulatory element is the WPRE [SEQ ID NO 11].

In a preferred embodiment of the invention said vector nucleic acid molecule as set forth in i)-vi) above is single stranded or double stranded nucleic acid.

In a preferred embodiment of the invention said mammalian genome is human.

In a preferred embodiment of the invention said nucleic acid molecule to be expressed encodes a therapeutic protein or peptide.

In a preferred embodiment of the invention said therapeutic protein is Cas9, Cas9n, hSpCas9 or hSpCas9n.

In a preferred embodiment of the invention said therapeutic protein or peptide triggers a death signal.

Examples of proteins or peptides that trigger a cellular death signal are known in the art. For example Bacterial toxins such as the cholera toxin or the diphtheria toxin, alpha toxin, anthrax toxin, exotoxin, pertussis toxin, shiga toxin, shiga-like toxin etc are known to induce cell death. Furthermore, apoptotic signals/proteins such as Fas, TNF, caspases (initiator caspases, caspase 2, 8, 9, 10, 11, 12, and effector caspases, caspase 3,6,7) etc. In addition enzymes that are able to convert a non-toxic drug into a toxic component: e.g. the herpes simplex virus thymidine kinase (HSVtk) converts the rather non-toxic drug ganciclovir (GCV) into the toxic triphosphate (HSVtk/GCV system). A further example is the *Escherichia coli* purine nucleoside phosphorylase (PNP)/fludarabine suicide gene system.

In a further preferred embodiment of the invention said therapeutic protein or peptide is the HSVtk.

In an alternative preferred embodiment of the invention said expressed nucleic acid molecule is a therapeutic nucleic acid molecule.

In a preferred embodiment of the invention said therapeutic nucleic acid is a siRNA or shRNA.

In an alternative preferred embodiment of the invention said therapeutic nucleic acid molecule is an antisense RNA oligonucleotide or antisense miRNA.

In a further preferred embodiment of the invention said therapeutic nucleic acid molecule is a miRNA.

In a further preferred embodiment of the invention said therapeutic nucleic acid molecule is a trans-splicing RNA.

In a further preferred embodiment of the invention said therapeutic nucleic acid molecule is a guide RNA, single-guide RNA, crRNA, or tracrRNA.

In a preferred embodiment of the invention said therapeutic nucleic acid molecule is a transsplicing RNA.

In an alternative preferred embodiment of the invention said therapeutic nucleic acid molecule is a pre-mRNA or mRNA.

In a further preferred embodiment of the invention said minimal transcription promoter is derived from an RNA polymerase III promoter.

In a preferred embodiment of the invention said RNA polymerase III promoter is a U6 promoter and comprises a nucleotide sequences as set forth in SEQ ID NO: 1.

In an alternative preferred embodiment of the invention said RNA polymerase III promoter is a H1 promoter comprising a nucleotide sequence as set forth in SEQ ID NO: 2.

In an alternative preferred embodiment of the invention said RNA polymerase III promoter is a minimal H1 (mH1) promoter comprising a nucleotide sequence as set forth in SEQ ID NO: 3.

In a further alternative preferred embodiment of the invention said RNA polymerase III promoter is a modified mH1 promoter that includes a restriction endonuclease cleavage site and/or an inverted polymerase III transcriptional terminator comprising a nucleotide sequence as set forth in SEQ ID NO: 4.

In a further preferred embodiment of the invention said minimal transcription promoter is derived from an RNA polymerase II promoter.

In a preferred embodiment of the invention said RNA polymerase II promoter is a CMV promoter and comprises a nucleotide sequences as set forth in SEQ ID NO: 5.

In a preferred embodiment of the invention said transcription terminator nucleotide sequence is a RNA polymerase II or RNA polymerase III termination sequence.

In a preferred embodiment of the invention said RNA polymerase III termination sequence comprises one or more motifs comprising the nucleotide sequence TTTTT.

In a preferred embodiment of the invention said DNA nuclear targeting sequence comprises the nucleotide sequence set forth in SEQ ID NO: 6 (DTSα and/or SEQ ID NO: 7 (DTSβ).

In a preferred embodiment of the invention said enhancer nucleotide sequence comprises the nucleotide sequence set forth in SEQ ID NO: 8 (minimal enhancer: mSV40enh).

In a further preferred embodiment of the invention said enhancer nucleotide sequence comprises the nucleotide sequence set forth in SEQ ID NO: 9 (full length enhancer: fSV40enh).

In a further preferred embodiment of the invention said intron comprises the nucleotide sequence set forth in SEQ ID NO: 10.

In a further preferred embodiment of the invention said vector further encodes a detectable marker.

In a preferred embodiment of the invention said detectable marker is a fluorescence marker.

In a preferred embodiment of the invention said fluorescence marker is a fluorescent reporter protein.

The analysis of promoter activity in a tissue can be conveniently monitored by fusing a promoter to a nucleic acid that encodes a "reporter" protein or polypeptide. Examples are well known in the art and include enzymes such as β glucuronidase. Reporters that are proteinaceous fluorophores are also known in the art. Green fluorescent protein, GFP, is a spontaneously fluorescent protein isolated from coelenterates, such as the Pacific jellyfish, *Aequoria victoria*. Its role is to transduce, by energy transfer, the blue chemiluminescence of another protein, aequorin, into green fluorescent light. GFP can function as a protein tag, as it tolerates N- and C-terminal fusions to a broad variety of proteins many of which have been shown to retain native function. Most often it is used in the form of enhanced GFP in which codon usage is adapted to the human code. Other proteinaceous fluorophores include yellow, red and blue fluorescent proteins. These are commercially available from, for example, Clontech (www.clontech.com). A yet further example is firefly luciferase.

In a preferred embodiment of the invention wherein said nucleotide sequence with homology to a part of a mammalian genome is implemented into the double-stranded DNA part of the dumbbell vector.

In an alternative preferred embodiment of the invention said nucleotide sequence with homology to a part of a mammalian genome comprises a single-stranded loop of the dumbbell vector.

According to a further aspect of the invention there is provided a pharmaceutical composition comprising a dumbbell-shaped vector according to the invention.

The dumbbell-shaped vector compositions of the present invention are administered in pharmaceutically acceptable preparations. Such preparations may routinely contain pharmaceutically acceptable concentrations of salt, buffering agents, preservatives, compatible carriers and supplementary therapeutic agents'. The dumbbell shaped vector compositions of the invention can be administered by any conventional route, including injection or by gradual infusion over time. The administration may, for example, intravenous, intraperitoneal, intramuscular, intracavity, subcutaneous, transdermal, oral, topical, intratracheal, nasal, intravaginal or trans-epithelial. Alternatively, the dumbbell-shaped vector or vector composition of this invention is delivered by physical methods including but not limited to liquid jet-injection, microinjection, microneedles, powder particle injection, gold particle injection, gene gun, electroporation or hydrodynamic injection.

The dumbbell-shaped vector compositions of the invention are administered in effective amounts. An "effective amount" is that amount of the dumbbell-shaped vector that alone, or together with further doses, produces the desired response. In the case of treating a disease, the desired response is inhibiting the progression of the disease. This may involve only slowing the progression of the disease temporarily, although more preferably, it involves halting the progression of the disease permanently. This can be monitored by routine methods. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The dumbbell-shaped vector compositions used in the foregoing methods preferably are sterile and contain an effective amount of dumbbell-shaped vector according to the invention for producing the desired response in a unit of weight or volume suitable for administration to a patient. The doses of vector administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. Other protocols for the administration of vector compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the dumbbell-shaped vector compositions of the invention are applied in pharmaceutically-acceptable amounts and in pharmaceutically-acceptable compositions. The term "pharmaceutically acceptable" means a non-toxic material that does not interfere with the effectiveness of the biological activity of the active agent.

Such preparations may routinely contain salts, buffering agents, preservatives, compatible carriers, and optionally other therapeutic agents' (e.g. those typically used in the treatment of the specific disease indication). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions containing dumbbell-shaped vectors according to the invention may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The dumbbell-shaped vector compositions may conveniently be presented in unit dosage form and may be prepared by any of the methods well-known in the art of pharmacy. All methods include the step of bringing the active agent into association with a vector which constitutes one or more accessory ingredients. Compositions containing vectors according to the invention may be administered as aerosols and inhaled. Compositions suitable for parenteral administration conveniently comprise a sterile aqueous or non-aqueous preparation of the vectors, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butanediol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, PA.

In an alternative embodiment of the invention said pharmaceutical composition is a DNA vaccine composition comprising an adjuvant and/or carrier.

According to an aspect of the invention there is provided a method to generate a dumbbell-shaped dual expression vector comprising two expression cassettes wherein said vector comprises:

i) providing a preparation comprising a first single stranded nucleic acid template comprising a target nucleic acid molecule comprising the reverse complement of a first transcriptional promoter at the 5' terminal sequence and the sequence of a second transcriptional terminator at the 3' terminal sequence;

ii) contacting said first single stranded nucleic acid template with an first oligonucleotide primer comprising a 5'-phosphate and a 3'-hydroxyl group that is complementary to at least part of the 3' terminal nucleotide sequence of said single stranded nucleic acid template and further comprising a 5' nucleotide sequence not complementary to the target nucleic acid molecule wherein said oligonucleotide primer comprises a first sequence of interest to be transcribed and further comprising the reverse complement sequence of a first transcriptional terminator and further comprising a modified nucleotide sequence that prevents extension of the 5' nucleotide sequence not complementary to the target nucleic acid molecule;

iii) providing polymerase chain reaction components and primer extending the 3' annealed oligonucleotide primer to form a second template;

iv) contacting said second template with a second oligonucleotide primer comprising a 5'-phosphate and a 3'-hydroxyl group that is complementary to at least part of the 3' terminal nucleotide sequence of said second template and further comprising a 5' nucleotide sequence not complementary to the second template wherein said oligonucleotide primer comprises a second sequence of interest to be transcribed and further comprising the reverse complement sequence of a second transcriptional terminator and further comprising a modified nucleotide sequence that prevents extension of the 5' nucleotide sequence not complementary to the second template;

v) providing polymerase chain reaction components and primer extending the 3' annealed oligonucleotide primer to form a double stranded nucleic acid;

vi) polymerase chain amplify the double stranded nucleic acid to synthesize a pool of template DNA and annealing said templates to create double stranded nucleic acid comprising a 5' nucleotide sequence not complementary to the target nucleic acid molecule; and vii) contacting the annealed template nucleic acid with a 5 DNA ligase to link the terminal 5'-phosphate of the non-complementary 5' nucleotide sequence to the 3'-OH of said amplified template nucleic acid to create a terminal loop structure.

In a preferred method of the invention said target nucleotide acid molecule comprises the sequence of a transcriptional promoter at its 3' terminal nucleotide sequence and further comprises the reverse complement sequence of a transcriptional promoter at its 5' terminal nucleotide sequence.

In a further preferred method said transcriptional promoter is a polymerase III promoter.

In a further preferred method said polymerase III promoter is the U6 promoter.

In a further preferred method said polymerase III promoter is the H1 promoter.

In a further preferred method said polymerase III promoter is the H1 promoter.

In an alternative preferred method said transcription promoter is a polymerase II promoter.

In a further preferred method said polymerase II promoter is the CMV promoter.

In a preferred method of the invention said oligonucleotide primer comprises a nucleotide sequence that is non-complementary with said target nucleic acid molecule but includes a region of internal complementarity over part of its length that forms a stem loop structure.

In a preferred method of the invention said oligonucleotide primer includes a palindromic nucleotide sequence over part of its length.

In a preferred method of the invention said oligonucleotide primer modification is the inclusion of a site that is not recognised as template for base-pairing during primer extension by the DNA polymerase in said primer.

In a preferred method of the invention said oligonucleotide primer modification is the inclusion of an abasic site in said primer.

Abasic sites are occurring naturally typically caused by DNA damage or through spontaneous mutation and define a location in DNA or RNA that has neither a purine nor a pyrimidine base. The sites are referred to as apurinic or apyrimidinic.

In a further preferred method said abasic site is an apurinic/apyrimidinic site.

In a further preferred method said apurinic/apyrimidinic sites comprise a tetrahydrofuran.

In a further preferred method said abasic site comprises at least one or at least three apurinic/apyrimidinic sites.

In a further preferred method said abasic site contains one apurinic/apyrimidinic site.

In a further preferred method of the invention said abasic site separates the region complementary to the 3' terminal nucleotide sequence of said single stranded nucleic acid template and the 5' nucleotide sequence not complementary to the target nucleic acid molecule.

In a preferred method of the invention said oligonucleotide primer comprises a non-complementary nucleotide sequence comprising a transcriptional terminator.

In a further preferred method of the invention said transcriptional terminator polymerase III transcriptional terminator.

In a further preferred method said polymerase III transcriptional terminator is a small poly thymidine (T) stretch.

In a further preferred method said polymerase III transcriptional terminator is a T pentamer.

In an alternative preferred method of the invention said transcriptional terminator is a polymerase II transcriptional terminator.

In a further preferred method said polymerase II transcriptional terminator is the SV40 polyadenylation site.

In a preferred method of the invention said oligonucleotide primer comprises a sequence of interest to be transcribed.

In a further preferred method of the invention said sequence of interest is a non-protein-coding sequence.

In an alternative preferred method of the invention said sequence of interest is a protein-coding sequence.

In a preferred method of the invention said DNA ligase is a phage DNA ligase, for example a T4 DNA ligase or *E. coli* DNA ligase.

In an alternative preferred method of the invention said DNA ligase is a circligase.

According to an aspect of the invention there is provided a cloning-free and endonuclease-free method to generate a dumbbell-shaped vector that includes a hairpin-structured expression cassette comprising:

i) providing a preparation comprising a single stranded nucleic acid template comprising a target nucleic acid molecule comprising two complementary sequence segments wherein each segment comprises a transcription promoter sequence and further comprises a transcriptional terminator and wherein said two complementary sequence segments are separated by a third sequence segment;

ii) providing a preparation wherein said single stranded nucleic acid template additionally comprises a stem;

iii) contacting said single stranded nucleic acid template with a first oligonucleotide primer comprising a 3'-hydroxyl group that is complementary to at least part of the 3' terminal nucleotide sequence of said single stranded nucleic acid template and further comprising a 5' nucleotide sequence not complementary to the target nucleic acid molecule wherein said oligonucleotide primer comprises the sequence coding for the 3' arm of a hairpin-structured RNA and further contacting said single stranded nucleic acid template with a first blocking oligonucleotide that is complementary to at least part of the 5' terminal nucleotide sequence of said single stranded nucleic acid template;

iv) providing polymerase chain reaction components to primer extend the 3' annealed first oligonucleotide primer;

v) contacting said extended oligonucleotide primer with a second oligonucleotide primer comprising a 3'-hydroxyl group that is complementary to at least part of the 3' terminal nucleotide sequence of said extended oligonucleotide primer and further comprising a 5' nucleotide sequence not complementary to the target nucleic acid molecule wherein said oligonucleotide primer comprises the sequence coding for the 3' arm of a hairpin-structured RNA and further contacting said single stranded nucleic acid template with a second blocking oligonucleotide that is complementary to at least part of the 5' terminal nucleotide sequence of said extended oligonucleotide primer;

vi) polymerase chain amplify the template to synthesize a pool of template DNA and annealing said templates to create double stranded nucleic acid comprising a sequence coding for the 3' arm of a hairpin-structured RNA at the 5' nucleotide sequences of the plus strand and the minus strand and comprising a sequence coding for the 5' arm of a hairpin-structured RNA at the 3' nucleotide sequences of the plus strand and the minus strand;

vii) heat denature said double stranded nucleic acid and then cool down to allow intra-molecular refolding of the resulting plus strand and minus strand DNA to create preformed oligomeric stem-loop structures comprised of plus or minus strand DNA;

viii) contacting said preformed oligomeric loops structures of plus strand and minus strand DNA with a DNA ligase to link the terminal 5'-phosphorylated 5' overhang to the terminal 3'-OH group of the 3' overhang of the same DNA strand in an intramolecular ligation to create covalently closed plus strand-derived and minus strand-derived dumbbell-shaped vector DNA comprising hairpin-structured template DNA for the transcription of hairpin-structured RNA;

ix) contacting said dumbbell-shaped vector DNA with a DNA exonuclease to remove all primers and non-covalently closed DNA that harbours 5' and 3' ends.

In a preferred method said transcription promoter is a polymerase III promoter.

In a further preferred method said polymerase III promoter is the U6 promoter.

In a further preferred method said polymerase III promoter is the H1 promoter.

In a further preferred method said polymerase III promoter is the minimal H1 promoter.

In an alternative preferred method said transcription promoter is a polymerase II promoter.

In a further preferred method said polymerase II promoter is the CMV promoter.

In a preferred method said transcriptional terminator is a polymerase III transcriptional terminator.

In a further preferred method said polymerase III transcriptional terminator is a small poly thymidine (T) stretch.

In a further preferred method said polymerase III transcriptional terminator is a T pentamer.

In an alternative preferred method said transcriptional terminator is a polymerase II transcriptional terminator.

In a further preferred method said polymerase II transcriptional terminator is the SV40 polyadenylation site.

In a preferred method said stem is an artificial stem.

In a further preferred method said stem is a microRNA (miRNA) stem.

In a further preferred method said stem is a miRNA stem is a miRNA-30 (miR-30) stem.

In a preferred method said third sequence segment is an oligomeric DNA sequence.

In a further preferred method said third sequence segment is a tetrameric DNA sequence.

In a further preferred method said third sequence segment is a T tetramer.

In a preferred method said first oligonucleotide primer comprises a 5' phosphate.

In a preferred method said hairpin-structured RNA is a small hairpin RNA (shRNA).

In a further preferred method said hairpin-structured RNA is a precursor miRNA (pre-miRNA).

In a preferred method said first blocking oligonucleotide is complementary to the complete 5' terminal nucleotide sequence half of said single stranded nucleic acid template.

In a preferred method said second oligonucleotide primer comprises a 5' phosphate.

In a preferred method said second blocking oligonucleotide is complementary to the complete 5' terminal nucleotide sequence half of said extended oligonucleotide primer.

In a preferred method said heat denaturing comprises an incubation at 96° C. for 5 min.

In a preferred method said cooling down comprises a gradual cooling down from 96° C. to room temperature.

In a preferred method of the invention said ligase is a single strand DNA-specific ligase.

In a further preferred method of the invention said ligase is the CircLigase.

In a preferred method of the invention said exonuclease is the T7 DNA polymerase.

According to an aspect of the invention there is provided a cloning-free and endonuclease-free method to generate a dumbbell-shaped vector that includes an expression cassette comprising:

i) providing a preparation comprising a single stranded nucleic acid template comprising a target nucleic acid molecule comprising two complementary sequence segments wherein each segment comprises a transcription promoter sequence and further comprises a transcriptional terminator and wherein said two complementary sequence segments are separated by a third sequence segment;

ii) providing a preparation wherein said single stranded nucleic acid template additionally comprises a stem;

iii) contacting said single stranded nucleic acid template with a first oligonucleotide primer comprising a 3'-hydroxyl group that is complementary to at least part of the 3' terminal nucleotide sequence of said single stranded nucleic acid template and further comprising a 5' nucleotide sequence not complementary to the target nucleic acid molecule and further contacting said single-stranded nucleic acid with a first set of blocking oligonucleotides comprising one, two, three or more oligonucleotides that are complementary to at least part of the 5' terminal nucleotide sequence of said single stranded nucleic acid template;

iv) providing polymerase chain reaction components to primer extend the 3' annealed first oligonucleotide primer;

v) contacting said extended oligonucleotide primer with a second oligonucleotide primer comprising a 3'-hydroxyl group that is complementary to at least part of the 3' terminal nucleotide sequence of said extended oligonucleotide primer and further comprising a 5' nucleotide sequence not complementary to the target nucleic acid molecule and further contacting said single stranded nucleic acid template with a second set of blocking oligonucleotides comprising one, two, three or more oligonucleotides that are complementary to at least part of the 5' terminal nucleotide sequence of said extended oligonucleotide primer;

vi) polymerase chain amplify the template to synthesize a pool of extended oligonucleotide primers (and annealing said templates to create double stranded nucleic acid comprising a sequence coding for the 3' arm of a hairpin-structured RNA at the 5' nucleotide sequences of the plus strand and the minus strand and comprising a sequence coding for the 5' arm of a hairpin-structured RNA at the 3' nucleotide sequences of the plus strand and the minus strand)

vii) contacting said pool of extended oligonucleotide primers with a third oligonucleotide primer comprising a 3' hydroxyl group that is complementary to at least part of the 3' terminal nucleotide sequence of the oligonucleotide primer extended by said first oligonucleotide primer and further comprising a 5' nucleotide sequence not complementary to said extended oligonucleotide primer and further contacting said pool of extended oligonucleotide primers with a fourth oligonucleotide primer comprising a 3' hydroxyl group that is complementary to at least part of the 3' terminal nucleotide sequence of the oligonucleotide primer extended by said second oligonucleotide primer and further comprising a 5' nucleotide sequence not complementary to said extended oligonucleotide primer and further contacting said extended oligonucleotide primers with said first and second set of blocking oligonucleotides;

viii) repeating steps iv) and vii) using a fifth and sixth, seventh and eight or more pairs of oligonucleotide primers wherein the last set of primers comprises 3' hydroxyl groups and 5' phosphate groups;

ix) polymerase chain amplify the template to synthesize a pool of extended oligonucleotide primers and annealing said templates to create double stranded nucleic acid comprising a sequence coding for the 3' arm of a hairpin-structured RNA at the 5' nucleotide sequences of the plus strand and the minus strand and comprising a sequence coding for the 5' arm of a hairpin-structured RNA at the 3' nucleotide sequences of the plus strand and the minus strand;

x) heat denature said double stranded nucleic acid and then cool down to allow intra-molecular refolding of the resulting plus strand and minus strand DNA to create preformed oligomeric stem-loop structures comprised of plus or minus strand DNA;

xi) contacting said preformed oligomeric loops structures of plus strand and minus strand DNA with a DNA ligase to link the terminal 5'-phosphorylated 5' overhang to the terminal 3'-OH group of the 3' overhang of the same DNA strand in an intramolecular ligation to create covalently closed plus strand-derived and minus strand-derived dumbbell-shaped vector DNA comprising hairpin-structured template DNA for the transcription of hairpin-structured RNA;

xii) contacting said dumbbell-shaped vector DNA with a DNA exonuclease to remove all primers and non-covalently closed DNA that harbours 5' and 3' ends.

In a preferred method said transcription promoter is a polymerase III promoter.

In a further preferred method said polymerase III promoter is the U6 promoter.

In a further preferred method said polymerase III promoter is the H1 promoter.

In a further preferred method said polymerase III promoter is the minimal H1 promoter.

In an alternative preferred method said transcription promoter is a polymerase II promoter.

In a further preferred method said polymerase II promoter is the CMV promoter.

In a preferred method said stem is an artificial stem.

In a further preferred method said stem is a microRNA (miRNA) stem.

In a further preferred method said stem is a miRNA stem is a miRNA-30 (miR-30) stem.

In a preferred method said third sequence segment is an oligomeric DNA sequence.

In a further preferred method said third sequence segment is a tetrameric DNA sequence.

In a further preferred method said third sequence segment is a T tetramer.

In an alternative preferred method said first and said second oligonucleotide primers comprise the reverse complement sequence of a translational start codon CAT in their 5' nucleotide sequence not complementary to the target nucleic acid molecule.

In a further preferred method the primers of said last set of primers comprise the reverse complement sequence of a translational stop codon in their 5' nucleotide sequence not complementary to said extended oligonucleotide primer.

In a further preferred method said translational stop codon is TAG, TAA, or TGA.

In alternative preferred method the primers of said last set of primers comprise the reverse complement sequence of a transcriptional terminator in their 5' nucleotide sequence not complementary to said extended oligonucleotide primer.

In a preferred method said transcriptional terminator is a polymerase III transcriptional terminator.

In a further preferred method said polymerase III transcriptional terminator is a small poly thymidine (T) stretch.

In a further preferred method said polymerase III transcriptional terminator is a T pentamer.

In an alternative preferred method said transcriptional terminator is a polymerase II transcriptional terminator.

In a further preferred method said polymerase II transcriptional terminator is the SV40 polyadenylation site.

In an alternative preferred method said first oligonucleotide primer comprises a 5' phosphate.

In a preferred method said hairpin-structured RNA is a small hairpin RNA (shRNA).

In a further preferred method said hairpin-structured RNA is a precursor miRNA (pre-miRNA).

In a preferred method said first blocking oligonucleotide is complementary to the complete 5' terminal nucleotide sequence half of said single stranded nucleic acid template.

In a preferred method said second oligonucleotide primer comprises a 5' phosphate.

In a preferred method said second blocking oligonucleotide is complementary to the complete 5' terminal nucleotide sequence half of said extended oligonucleotide primer.

In a preferred method said heat denaturing comprises an incubation at 96° C. for 5 min.

In a preferred method said cooling down comprises a gradual cooling down from 96° C. to room temperature.

In a preferred method of the invention said ligase is a single strand DNA-specific ligase.

In a further preferred method of the invention said ligase is the CircLigase.

In a preferred method of the invention said exonuclease is the T7 DNA polymerase.

According to an aspect of the invention there is provided a dumbbell-shaped vector synthesized by the method according to the invention.

According to a further aspect of the invention there is provided a method for the transfection of primary cells isolated from a human subject comprising:
i) providing an isolated sample comprising cells to be transfected;
ii) forming a preparation comprising said isolated cell sample and contacting said sample with a dumbbell-shaped vector according to the invention;
iii) providing transformation conditions that enable introduction of said dumbbellshaped vector into said primary cell sample and sustained expression of a nucleic acid molecule included in said vector.

According to a further aspect of the invention there is provided an ex vivo method to treat a patient suffering from a disease that would benefit from gene therapy comprising the steps:
i) obtaining a sample from said subject comprising cells to be transfected;
ii) forming a cell culture preparation comprising a dumbbell-shaped vector according to the invention and providing conditions to transfect said vector into said cells; and
iii) administering the transfected cells to said subject.

In a preferred method of the invention said isolated sample comprises stem cells.

In a preferred embodiment of the invention said stem cells are selected from the group consisting of: pluripotent stem cells, for example embryonic stem cells or induced pluripotent stem cells, multipotent stem cells, lineage restricted stem cells.

The term "stem cell" represents a generic group of undifferentiated cells that possess the capacity for self-renewal while retaining varying potentials to form differentiated cells and tissues. Stem cells can be pluripotent or multipotent. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Examples of multipotent stem cells include mesenchymal stem cells. Mesenchymal stem cells or MSCs differentiate into a variety of cell types that include osteoblasts, chondrocytes, myocytes, adipocytes and neurones. Typically, MSCs are obtained from bone marrow but can originate from other sources such as adipose tissue.

In a preferred method of the invention said cells are peripheral blood mononuclear cells.

In a preferred method of the invention said peripheral blood mononuclear cells includes: Tlymphocytes, [either or both $CD8_+$ T lymphocytes or $CD4_+$ T lymphocytes] B lymphocytes, Dendritic Cells, T Regulatory Cells, innate lymphoid cells or Natural Killer Cells [NK cells].

It will be apparent that "peripheral blood mononuclear cells" can be isolated from sources other than blood, for example lymph nodes and spleen, and reference to peripheral blood mononuclear cells does not limit the invention to those cells isolated from blood.

According to a further aspect of the invention there is provided a kit comprising: an oligonucleotide primer designed to be complementary to at least part of the 3' terminal nucleotide sequence of a single stranded target nucleic acid template and further comprising a 5' nucleotide sequence not complementary to the target nucleic acid molecule wherein said oligonucleotide primer comprises a modified nucleotide sequence that prevents extension of the 5' nucleotide sequence not complementary to the target nucleic acid molecule when annealed to the target.

In a preferred embodiment of the invention said kit also comprises polymerase chain reaction components.

In a preferred embodiment of the invention said kit comprises: 5 a thermostable DNA polymerase, deoxynucleotide triphosphates and co-factors required for polymerase chain amplification.

In a preferred embodiment of the invention said kit includes a DNA ligase.

In a preferred embodiment of the invention said kit further comprises cell transfection components for the transfection of cells, preferably mammalian cells such human cells.

Specific Embodiments

Therapeutic Proteins & Peptides

The invention encompasses dumbbell-shape vectors comprising nucleic acids encoding pharmaceutical proteins such as "cytokines". Cytokines are involved in a number of diverse cellular functions. These include modulation of the immune system, regulation of energy metabolism and control of growth and development. Cytokines mediate their effects via receptors expressed at the cell surface on target cells. Examples of cytokines include the interleukins such as: IL1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and 33. Other examples include growth hormone, leptin, erythropoietin, prolactin, tumour necrosis factor [TNF], granulocyte colony stimulating factor (GCSF), granulocyte macrophage colony stimulating factor (GMCSF), ciliary neurotrophic factor (CNTF), cardiotrophin-1 (CT-1), leukemia inhibitory factor (LIF) and oncostatin M (OSM), interferon α, interferon β, interferon ε, interferon κ and ω interferon.

Examples of pharmaceutically active peptides include GLP-1, anti-diuretic hormone, oxytocin, gonadotropin releasing hormone, corticotrophin releasing hormone; calcitonin, glucagon, amylin, A-type natriuretic hormone, B-type natriuretic hormone, ghrelin, neuropeptide Y, neuropeptide $YY_{3-36}$, growth hormone releasing hormone, somatostatin, or homologues or analogues thereof.

The term "chemokine" refers to a group of structurally related low-molecular weight factors secreted by cells having mitogenic, chemotactic or inflammatory activities. They are primarily cationic proteins of 70 to 100 amino acid residues that share four conserved cysteine residues. These proteins can be sorted into two groups based on the spacing of the two amino-terminal cysteines. In the first group, the two cysteines are separated by a single residue (C-x-C), while in the second group they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-I and -II), pre-B cell growth stimulating factor (PBSF), and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 α (MIP-1-α), macrophage inflammatory protein 1β (MIP-1-β), macrophage inflammatory protein 1-γ (MIP-1-γ), macrophage inflammatory protein 3 α (MIP-3-α, macrophage inflammatory protein 3 β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3.

A number of growth factors have been identified which promote/activate endothelial cells to undergo angiogenesis. These include vascular endothelial growth factor (VEGF A); VEGF B, VEGF C, and VEGF D; transforming growth factor (TGFb); acidic and basic fibroblast growth factor (aFGF and bFGF); and platelet derived growth factor (PDGF). VEGF is an endothelial cell-specific growth factor which has a very specific site of action, namely the promotion of endothelial cell proliferation, migration and differentiation. VEGF is a complex comprising two identical 23 kD polypeptides. VEGF can exist as four distinct polypeptides of different molecular weight, each being derived from an alternatively spliced mRNA. bFGF is a growth factor that functions to stimulate the proliferation of fibroblasts and endothelial cells. bFGF is a single polypeptide chain with a molecular weight of 16.5 Kd. Several molecular forms of bFGF have been discovered which differ in the length at their amino terminal region. However the biological function of the various molecular forms appears to be the same.

Pro-drug activating polypeptides are also within the scope of the invention. The term prodrug activating genes refers to nucleotide sequences, the expression of which, results in the production of proteins capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine (5FC) to 5 fluorouracil (5FU), a potent antitumour agent. The lysis of the tumour cell provides a localized burst of cytosine deaminase capable of converting 5FC to 5FU at the localized point of the tumour resulting in the killing of many surrounding tumour cells. Additionally, the thymidine kinase (TK) gene (see U.S. Pat. Nos. 5,631,236 and 5,601,818) in which the cells expressing the TK gene product become susceptible to selective killing by the administration of ganciclovir may be employed. Other examples of pro-drug activating enzymes are nitroreductase and cytochrome p450's (e.g. CYP1A2, CYP2E1 or CYP3A4).

Therapeutic Antibodies

Dumbbell-shaped vectors according to the invention may comprise transcription cassettes including therapeutic antibodies or antibody fragments.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen. Antibodies from non-human animals provoke an immune response to the foreign antibody and its removal from the circulation. Both chimeric and humanised antibodies have reduced antigenicity when administered to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

Various fragments of antibodies are known in the art. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A Fab$_2$ fragment comprises two joined Fab fragments. When these two fragments are joined by the immunoglobulin hinge region, a F(ab')$_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* (1) or Janeway et al. *Immunobiology* (2). Molecular biology now allows direct synthesis (via expression in cells or chemically) of these fragments, as well as synthesis of combinations thereof. A fragment of an antibody or immunoglobulin can also have bispecific function as described above.

RNA-Guided Genome Editing

RNA-guided genome editing is based on RNA-mediated adaptive defense systems evolved from bacteria and archaea termed clustered regulatory interspaced short palindromic repeats (CRISPR)/CRISPR-associated (Cas) systems which originally use short RNAs to direct degradation of foreign invading DNA originating from viruses or plasmids. The most common system is the *Streptococcus pyogenes* (SP) type II CRISPR system. For editing of genomic DNA in human cells several system adaptations were made: 1. The originally distinct two short RNA molecules, called CRISPR RNA (crRNA) and trans-activating crRNA (tracrRNA), necessary to guide the enzyme to the DNA target in order to trigger cleavage were fused to form a single guide RNA (gRNA). The scaffolding tracrRNA domain, hereinafter referred to as Cas-interacting domain, can be fused to any crRNA domain, hereinafter referred to as DNA binding domain (BD). 2. Codon optimization converted the SPCas9 into the hSPCas9. 3. To reduce off-target editing, an aspartate-to-alanine substitution (D10A) was introduced to convert the DNA double-strand break (DSB) triggering hSPCas9 into the DNA nickase hSPCas9n. The DNA binding domain (20 to 17 nt in length) of the gRNA can now guide the gRNA-Cas9 complex to complementary/homologous DNA sites termed protospacer, hereinafter referred to as DNA target site, which has to be followed 3' by a second short identifier called PAM (protospacer adjacent motif) which is 5'-NGG for the system described here. The BD of the gRNA can overlap with the site to be edited, or should alternatively be in proximity to this site. hSPCas9 complexes will then trigger DSBs, hSPCas9n complexes trigger nicks. Two hSPCas9n complexes with different gRNAs and shifted target sites will be required to trigger a double nick. DSBs including double nicks induced by Cas9 or Cas9n will then activate one of two endogenous repair mechanisms: 1. In the error-prone non-homologous end-joining (NHEJ) pathway, the ends will be processed and rejoined which can result in random insertion/deletion (indel) mutations. 2. Alternatively, a repair template in form of a plasmid, PCR product or single stranded oligodeoxyribonucleotides (termed oligonucleotides in the following) can be supplied to leverage the homology-directed repair (HDR) pathway triggering high fidelity, precise editing. Single nicks trigger HDR using the intact strand as template.

Therapeutic Nucleic Acid

The invention encompasses dumbbell-shaped vectors expressing non-coding RNA including RNA aptamers, trans-splicing RNA (tsRNA), and inhibitory RNA complementary to a target mRNA sequence in a cell to ablate gene expression including antisense RNA (asRNA) or small or short hairpin RNA (shRNA) or small interfering RNA (siRNA) or microRNA (miRNA) or precursor miRNA (pre-miRNA) or antisense miRNA (as-miRNA).

The aptamer molecule folds into a structure that allows binding to a ligand which can be a small molecule, an amino acid, a cofactor, a peptide, a protein, a sugar, a lipid, a nucleotide or a nucleotide analogue.

The trans-splicing RNA molecule comprises three functional RNA sequence domains: Firstly, a target binding domain comprising one or more antisense RNA sequences complementary to one or more target precursor messenger RNA (pre-mRNA) sequences; secondly, a splicing domain comprising either a splice donor sequence or alternatively a splice acceptor sequence, a branch point and a polypyrimidine tract; thirdly, a coding sequence domain encoding a peptide or protein of interest. The trans-splicing RNA molecule can specifically bind to pre-mRNA target RNA and initiate a trans-splice reaction in which the coding sequence domain of the trans-splicing RNA is joint towards the target pre-mRNA leading to the formation of a chimeric RNA and enabling the expression of the coding sequence domain.

The shRNA molecule comprises two fully or partly complementary strands of RNA (a sense strand and an antisense strand) that are linked via a third stretch of RNA and wherein the sense and the antisense strands are annealed to each other to form a hairpin-structured RNA comprising a fully or partly base-paired stem and a single-stranded hairpin loop. After nuclear transcription, the shRNA mimics a primary miRNA transcript (pri-miRNA) or a pre-miRNA and is first processed by Drosha or directly exported from the nucleus into the cytoplasm of the cell via the Exportin-5-dependent nuclear export pathway. In the cytoplasm, the shRNA is processed by Dicer and a guide RNA is loaded into the RNA induced silencing complex (RISC) which specifically recognises and cleaves mRNA targets with a sufficient degree of complementarity to the guide RNA.

The siRNA molecule comprises two complementary strands of RNA (a sense strand and an antisense strand) annealed to each other to form a double stranded RNA molecule. The siRNA molecule is typically derived from exons of the gene which is to be ablated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

Pre-miRNA molecule comprises two fully or partly complementary strands of RNA (a 5' arm and a 3' arm of which either one or both comprise a mature miRNA) that are linked via a third stretch of RNA and wherein the sense and the antisense strands are annealed to each other to form a hairpin-structured RNA comprising a fully or partly base-paired stem and a single-stranded hairpin loop. After nuclear transcription, the pre-miRNA and is first processed by Drosha or directly exported from the nucleus into the cytoplasm of the cell via the Exportin-5-dependent nuclear export pathway. In the cytoplasm, the pre-miRNA is processed by Dicer and a mature miRNA is loaded into the RNA induced silencing complex (RISC) which specifically recognises and binds to mRNA targets that are complementary to 5' terminal positions 2 to 7 or 8 also termed seed region of the mature miRNA leading to translational block or cleavage of the mRNA target.

As used herein, the term "antisense oligonucleotide" or "antisense" describes an oligonucleotide that is an oligoribonucleotide or oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e. to hybridize substantially more to the target sequence than to any other sequence in the target cell under physiological conditions. In order to be sufficiently selective and potent for inhibition, such antisense oligonucleotides should comprise at least 7 (3) and more preferably, at least 15 consecutive bases which are complementary to the target. Most preferably, the antisense oligonucleotides comprise a complementary sequence of 20-30 bases.

The as-miRNA molecule is an asRNA complementary that is fully or partly complementary to a pri-miRNA target molecule, a pre-miRNA target molecule, a mature miRNA target or the seed region of a mature miRNA target. It is preferred that the as-miRNA molecule is complementary to the Dicer processing sites of a pri-miRNA or pre-miRNA target molecule.

DNA Vaccines/Adjuvants

The invention encompasses dumbbell-shaped vectors encoding antigenic polypeptides in the immunisation against diseases and pathogenic organisms. Typically DNA vaccines comprising dumbbell-shaped vectors include adjuvants and/or carriers to augment immune response to encoded antigens.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccines. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate has been used routinely in human vaccines. More recently, antigens incorporated into IRIV's (immunostimulating reconstituted influenza virosomes) and vaccines containing the emulsion-based adjuvant MF59 have been licensed in countries. Adjuvants can be classified according to their source, mechanism of action and physical or chemical properties. The most commonly described adjuvant classes are gel-type, microbial, oilemulsion and emulsifier-based, particulate, synthetic and cytokines. More than one adjuvant may be present in the final vaccine product. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds, PLG is a polymeric carbohydrate, virosomes can be derived from disparate viral particles, MDP is derived from bacterial cell walls; saponins are of plant origin, squalene is derived from shark liver and recombinant endogenous immunomodulators are derived from recombinant bacterial, yeast or mammalian cells.

There are several adjuvants licensed for veterinary vaccines, such as mineral oil emulsions that are too reactive for human use. Similarly, complete Freund's adjuvant, although being one of the most powerful adjuvants known, is not suitable for human use.

The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1. Basic scheme for universal template (UT)-assisted cloning-free dumbbell production. The universal DNA template is a double-stranded DNA that comprises an inverted repeat including all sequences required to express a coding or non-coding gene of interest such as a promoter, expression cassette, and transcriptional terminator. The inverted repeats are separated by a stretch of nucleotides. The protocol for dumbbell generation and purification comprises 4 steps. Step 1: PCR amplification of the universal template using 5'phosphorylated forward (Fw) and/or reverse (Rv) primers, both introducing either the antisense or sense strand of the sequence of interest; blocking oligos b1 and b2 are added into the reaction to suppress template refolding and to facilitate primer binding. Dotted lines represent plasmid sequences beyond the UT. Step 2: For dumbbell structure pre-folding, the PCR product is diluted, heat-denatured, and slowly cooled down to room temperature. Step 3: Dumbbell structures are covalently closed using a single-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: Cyan: (+) strand UT DNA; magenta: (−) minus strand UT DNA; grey: blocking oligos; green: sense (s) sequence; yellow: antisense (as) sequence.

Figure 2:
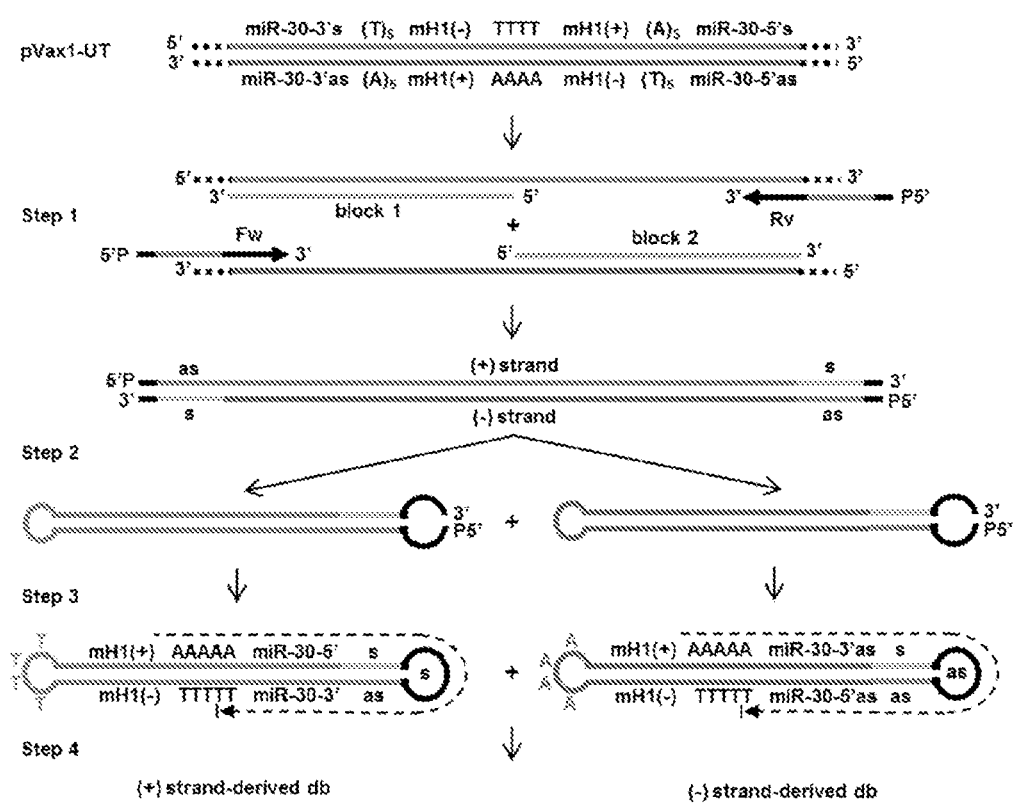

FIG. 2. Scheme for universal template (UT)-assisted cloning-free production of shRNA and miRNA expressing dumbbell vectors. The universal DNA template is a 262 bp double-stranded DNA that comprises an inverted repeat of the 99 bp minimal H1 promoter (mH1), a polymerase III transcriptional terminator ($T_5$), and the hsa-miR-30 precursor stem. The inverted repeats are separated by four T's (plus strand). The protocol for dumbbell generation and purification comprises 4 steps. Step 1: PCR amplification of the universal template using 5'phosphorylated forward (Fw) and/or reverse (Rv) primers, both introducing either the antisense or sense strand of a shRNA together with half of the shRNA loop sequence; blocking oligos b1 and b2 are added into the reaction to suppress template refolding and to facilitate primer binding. Dotted lines represent plasmid sequences beyond the UT. Step 2: For dumbbell structure pre-folding, the PCR product is diluted, heat-denatured, and slowly cooled down to room temperature. Step 3: Dumbbell structures are covalently closed using a single-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: Cyan: (+) strand UT DNA; magenta: (−) minus strand UT DNA; grey: blocking oligos; green: shRNA or miRNA sense (s) sequence; yellow: shRNA or miRNA antisense (as) sequence.

Figure 3:
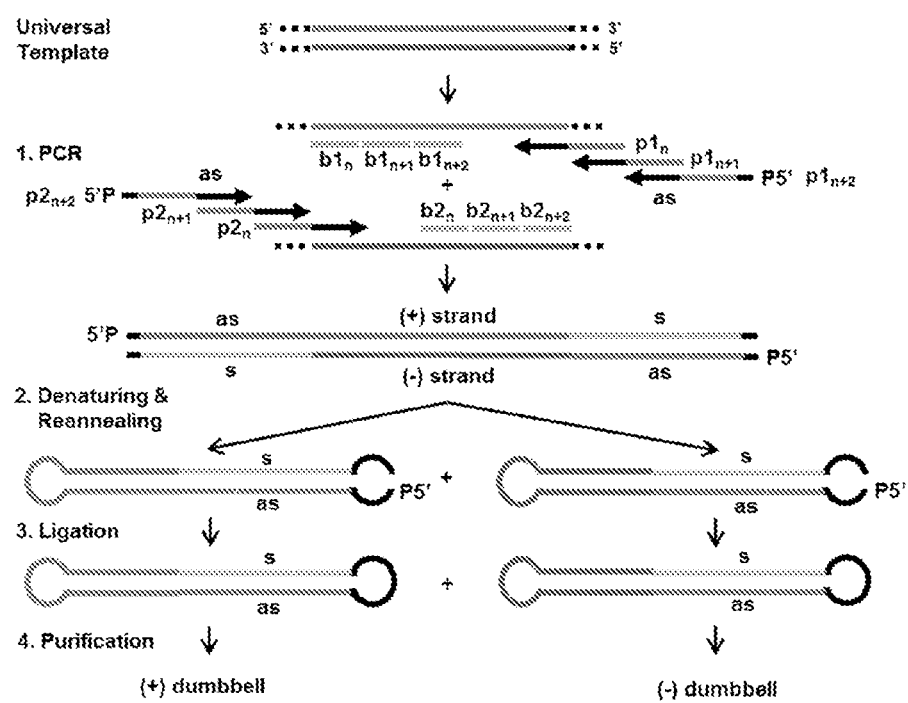

FIG. 3. Scheme for universal template (UT)-assisted cloning-free production of longer dumbbell vectors. The universal DNA template is a double-stranded DNA that comprises an inverted repeat including all sequences required to express a coding or non-coding gene of interest such as a promoter, expression cassette, and transcriptional terminator. The inverted repeats are separated by a stretch of nucleotides. The protocol for dumbbell generation and purification comprises 4 steps. Step 1: PCR amplification of the universal template using each a set of forward (Fw) and/or reverse (Rv) primers in which the respective outermost primers are 5'phosphorylated, both sets stepwise introducing either the antisense or sense strand of the sequence of interest; two set of blocking oligos $b1_{n+i}$ and $b2n_{+i}$ are added into the reaction to suppress template refolding and to facilitate primer binding. Dotted lines represent plasmid sequences beyond the UT. Step 2: For dumbbell structure pre-folding, the PCR product is diluted, heat-denatured, and slowly cooled down to room temperature. Step 3: Dumbbell structures are covalently closed using a single-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: Cyan: (+) strand UT DNA; magenta: (−) minus strand UT DNA; grey: blocking oligos; green: sense (s) sequence; yellow: antisense (as) sequence.

Figure 4:
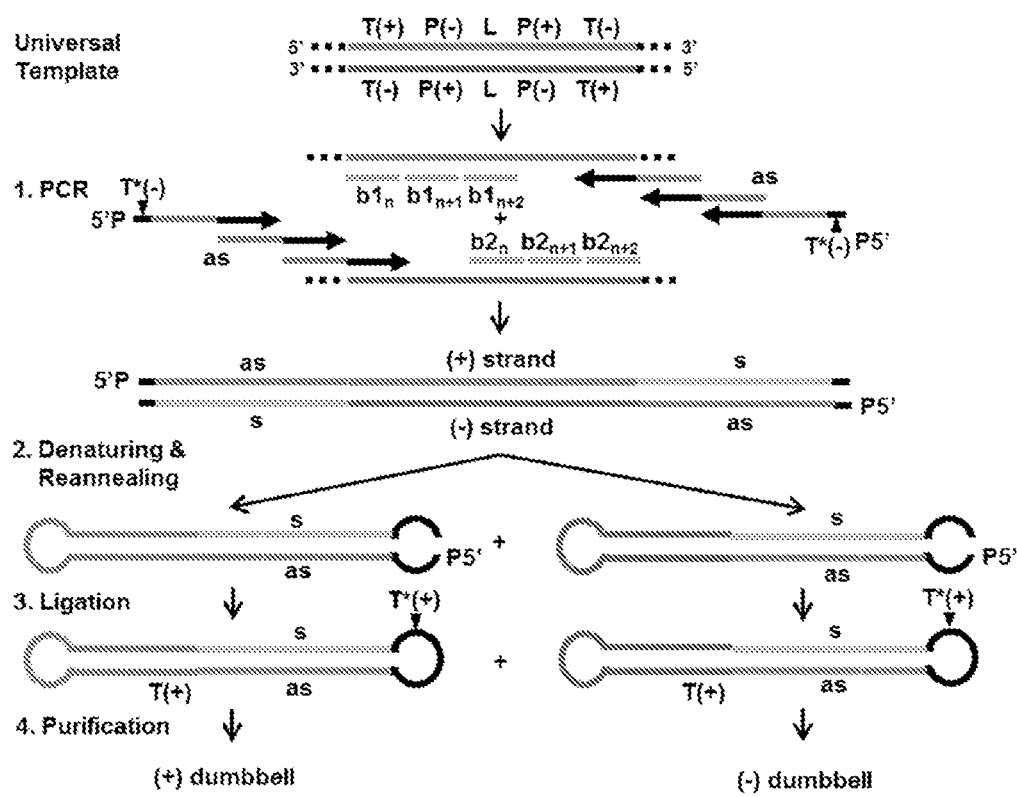

FIG. 4. Scheme for universal template (UT)-assisted cloning-free production of non-coding RNA expressing dumbbell vectors. The universal DNA template is a double-stranded DNA that comprises an inverted repeat including all sequences required to express a non-coding gene of interest such as a promoter, expression cassette, and transcriptional terminator. The inverted repeats are separated by a stretch of nucleotides. The protocol for dumbbell generation and purification comprises 4 steps. Step 1: PCR amplification of the universal template using each a set of forward (Fw) and/or reverse (Rv) primers in which the respective outermost primers are 5'phosphorylated and may introduce the reverse complement of a transcriptional terminator if non-palindromic sequences are to expressed, both sets stepwise introducing either the antisense or sense strand of the sequence of interest; two sets of blocking oligos are added into the reaction to suppress template refolding and to facilitate primer binding. Dotted lines represent plasmid sequences beyond the UT. Step 2: For dumbbell structure pre-folding, the PCR product is diluted, heat-denatured, and slowly cooled down to room temperature. Step 3: Dumbbell structures are covalently closed using a single-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: Cyan: (+) strand UT DNA; magenta: (−) minus strand UT DNA; grey: blocking oligos; green: sense (s) sequence; yellow: antisense (as) sequence.

Figure 5:
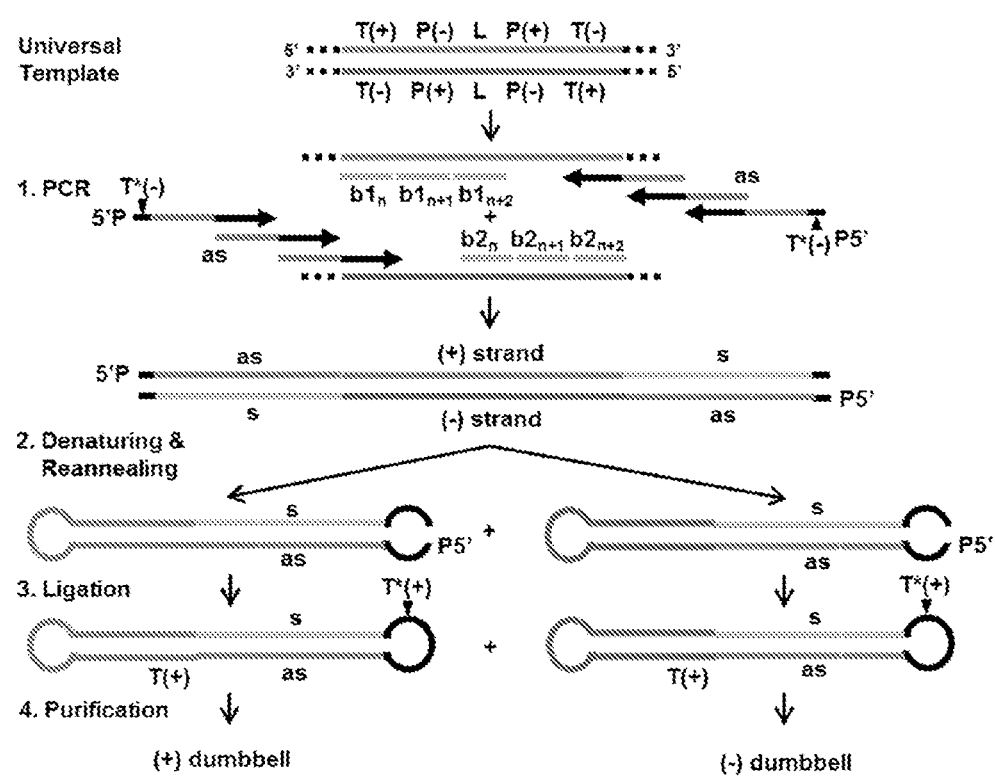

FIG. 5. Scheme for universal template (UT)-assisted cloning-free production of coding RNA expressing dumbbell vectors. The universal DNA template is a double-stranded DNA that comprises an inverted repeat including all sequences required to express a coding gene of interest such as a promoter, expression cassette, and transcriptional terminator. The inverted repeats are separated by a stretch of nucleotides. The protocol for dumbbell generation and purification comprises 4 steps. Step 1: PCR amplification of the universal template using each a set of forward (Fw) and/or reverse (Rv) primers in which the respective innermost primers introduce the reverse complement of a translational start codon (5'CAT3') and the respective outermost primers are 5'phosphorylated introducing the reverse complement of a translational stop codon, both sets stepwise introducing either the antisense or sense strand of the sequence of interest; two sets of blocking oligos $b1_{n+i}$ and $b2_{n+i}$ are added into the reaction to suppress template refolding and to facilitate primer binding. Dotted lines represent plasmid sequences beyond the UT. Step 2: For dumbbell structure pre-folding, the PCR product is diluted, heat-denatured, and slowly cooled down to room temperature. Step 3: Dumbbell structures are covalently closed using a single-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: Cyan: (+) strand UT DNA; magenta: (−) minus strand UT DNA; grey: blocking oligos; green: sense (s) sequence; yellow: antisense (as) sequence.

Figure 6:
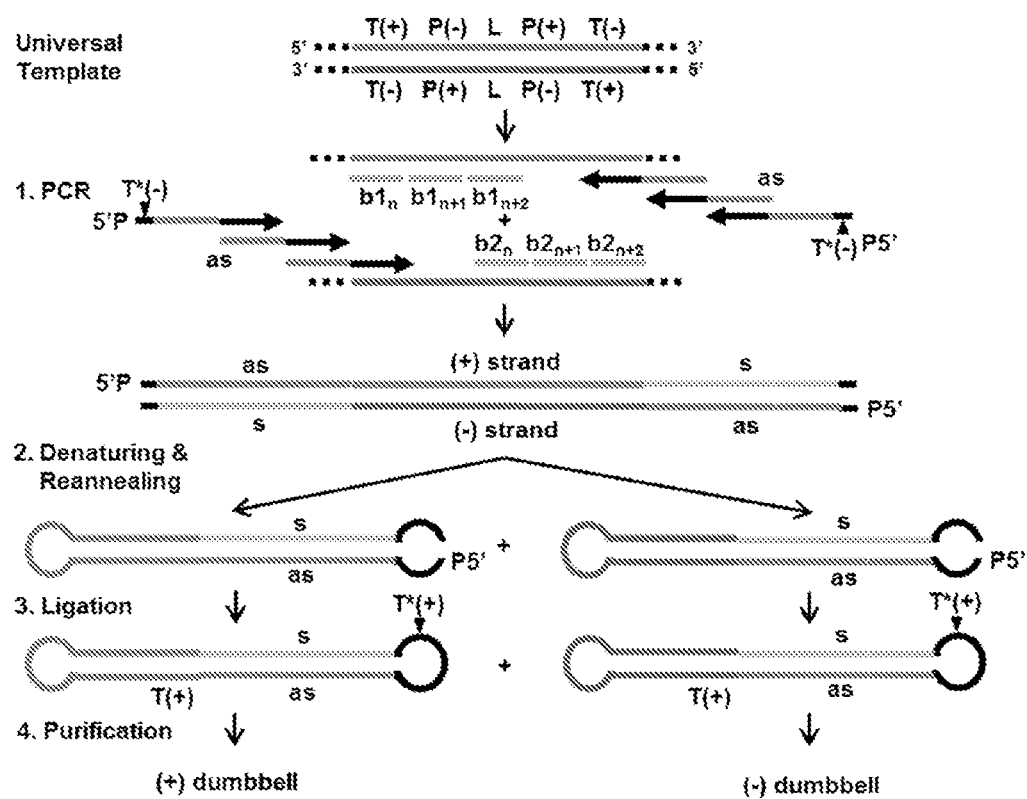

FIG. 6. Basic scheme for universal template (UT)-assisted cloning-free generation of dumbbell-shaped dual expression vectors. The universal DNA template is a double-stranded DNA that comprises two promoters, one in each strand and which are either identical or different, and potentially other regulatory sequences. The protocol for dumbbell generation and purification comprises 4 steps. Step 1: PCR amplification of the universal template using 5'phosphorylated forward (Fw) and/or reverse (Rv) primers, both introducing a sequence of interest (the same or different sequences), the reverse complement of a transcriptional terminator (same or different), one or multiple abasic positions (gap), and a 5'terminal sequence that is capable of forming a hairpin structure; blocking oligos b1 and b2 are added into the reaction to suppress template refolding and to facilitate primer binding. Dotted lines represent plasmid sequences beyond the UT. Step 2: For dumbbell structure pre-folding, the PCR reaction is cooled down to room temperature. Step 3: Dumbbell structures are covalently closed using a double-strand DNA ligase. Step 4: Treatment with T7 DNA polymerase removes oligos and non-ligated dumbbell DNA yielding covalently closed dumbbell vector DNA. Dotted arrows indicate transcribed sequences. All steps: cyan: UT DNA; yellow and green: Sequences of interest; magenta: abasic primer site (gap); grey: blocking oligos.

Figure 7:
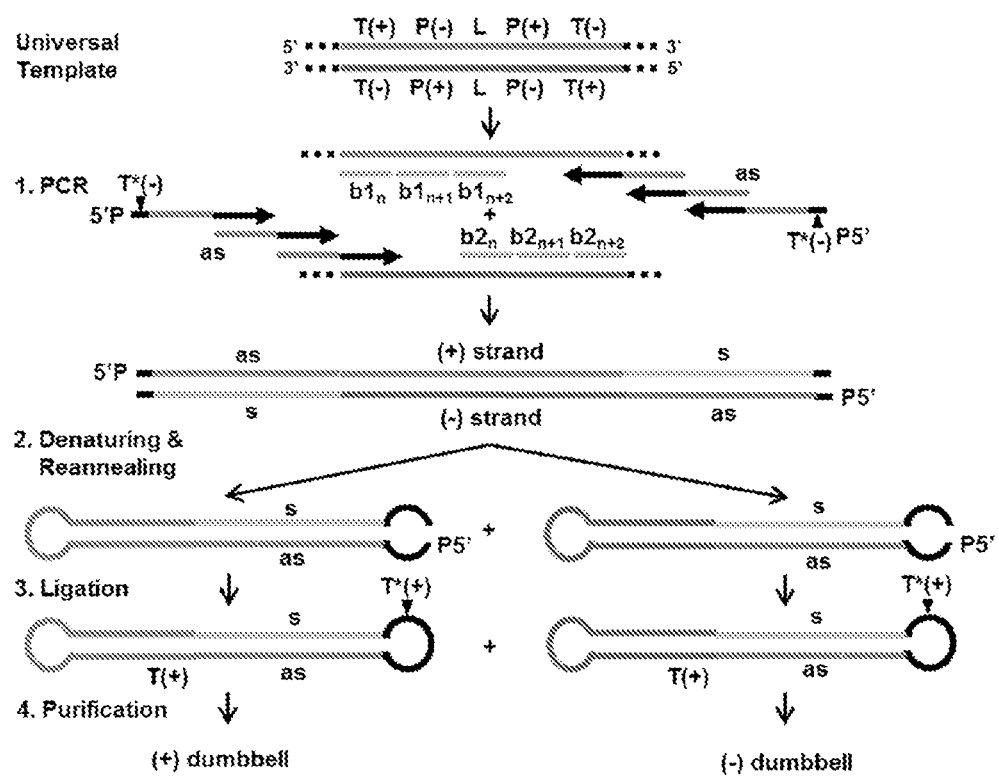

FIG. 7. Detailed scheme for universal template (UT)-assisted cloning-free generation of dumbbell-shaped dual expression vectors. The universal DNA template is a double-stranded DNA that comprises two promoters P1 and P2, one in each strand and which are either identical or different. The protocol for dumbbell generation and purification comprises 4 steps. Step 1: PCR amplification of the universal template using 5'phosphorylated forward (Fw) and/or reverse (Rv) primers, both introducing a sequence of interest SOI1 and SOI2 (the same or different sequences), the reverse complement of a transcriptional terminator T1(−) (same or different), one or multiple abasic positions (gap), and a 5'terminal sequence that is capable of forming a hairpin structure; blocking oligos b1 and b2 are added into the reaction to suppress template refolding and to facilitate primer binding. Dotted lines represent plasmid sequences beyond the UT. Step 2: For dumbbell structure pre-folding, the PCR reaction is cooled down to room temperature. Step 3: Dumbbell structures are covalently closed using a double-strand DNA ligase. Step 4: Treatment with T7 DNA polymerase removes oligos and non-ligated dumbbell DNA yielding covalently closed dumbbell vector DNA comprising two expression cassettes, P1(+)-SOI1-T1(+) and P2(+)-SOI2-T2(+), for expression of sequences of interest SOI1 and SOI2. Dotted arrows indicate transcribed sequences. All steps: cyan: UT DNA; yellow and green: Sequences of interest; magenta: abasic primer site (gap); grey: blocking oligos.

Figure 8:
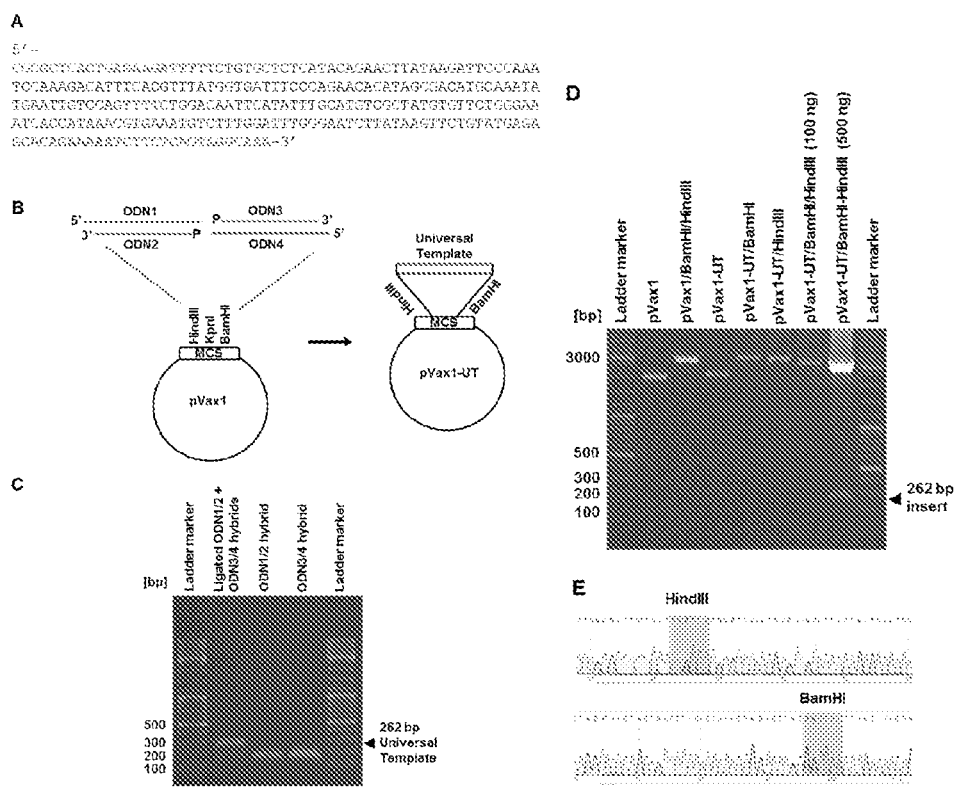

FIG. 8. Sequence, cloning and validation of universal template (UT). (A), UT plus strand sequence. Cyan: miR-30 5' and 3' stem; magenta: transcriptional terminator (sense and antisense); orange: loop-forming tetranucleotide sequence; black: mH1 sequence (sense and antisense). (B), UT cloning scheme. 5' phosphorylatyed oligos ODN2 and ODN3 were annealed with oligos ODN1 and ODN4, respectively. The resulting duplexes were ligated and the double-stranded UT sequence was cloned into pVax1 using the HindIII and BamHI restriction sites. Cyan: UT plus strand; magenta: UT minus strand. (C), Analytical 1% agarose gel electrophoresis showing the annealed oligo pairs ODN1/2 and ODN3/4 as well as the ligated hybrids. (D) Analytical HindIII and/or BamHI digestion and 1% agarose gel electrophoresis of the cloned plasmid pVax1-UT. HindIII/BamHI double digestion indicates the 262 bp UT band. (E), Sequencing of the HindIII and BamHI cloning sites of pVax1-UT.

Figure 9:
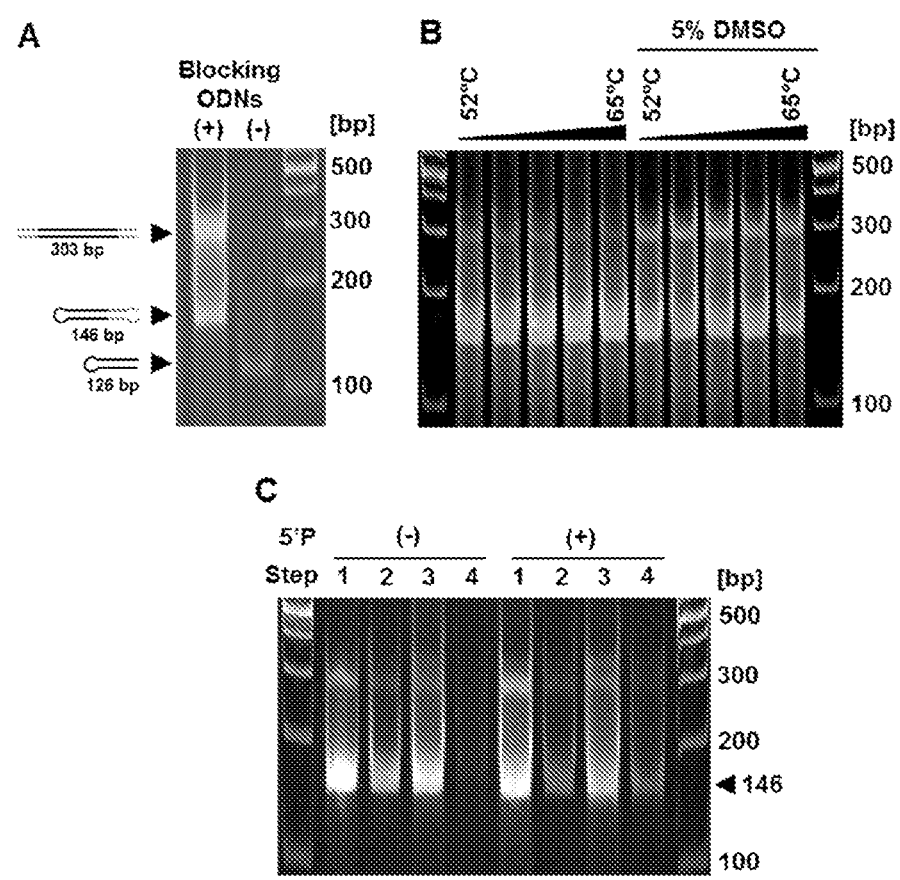

FIG. 9. PCR-based universal template (UT)-assisted dumbbell production. (A) PCR amplification of the UT depends on the addition of blocking oligos. Without adding blocking oligos (−), no PCR amplification was observed and only 126 bp refolded UT single-strands were detected. When adding blocking oligos (+), both the PCR-amplified double-stranded dumbbell DNA (303 bp) and refolded dumbbell single strands (146 bp) were detected. (B) Optimization of PCR conditions. PCR yield were virtually independent of the annealing temperature in the range between 52° C. and 65° C. Addition of 5% DMSO elevated the yields of double-stranded dumbbell DNA. (C) Assessment of DNA products referring to Steps 1 to 4 defined in FIG. 1. Step 1: PCR UT amplification yields double-stranded dumbbell DNA (303 bp) and re-folded dumbbell single strands (146 bp); Step 2: Heat-denaturation and refolding converts double-stranded dumbbell DNA into dumbbell single strands; Step 3: single-stranded DNA ligation covalently closes dumbbell vector DNA if 5'phosphorylated primers were used for PCR; Step 4: Exonuclease treatment removes un-ligated DNA and yields covalently closed dumbbell vectors (146 bp).

Figure 10:
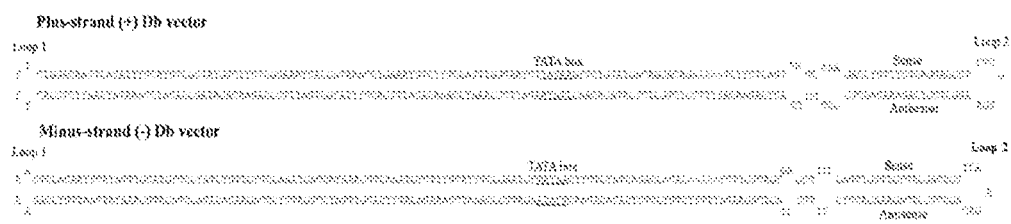

FIG. 10. Sequences and structures of the complete plus and minus strand-derived luciferase-targeting dumbbell vectors. The lamin NC-targeting vectors harbour the same dumbbell cores.

Figure 11:
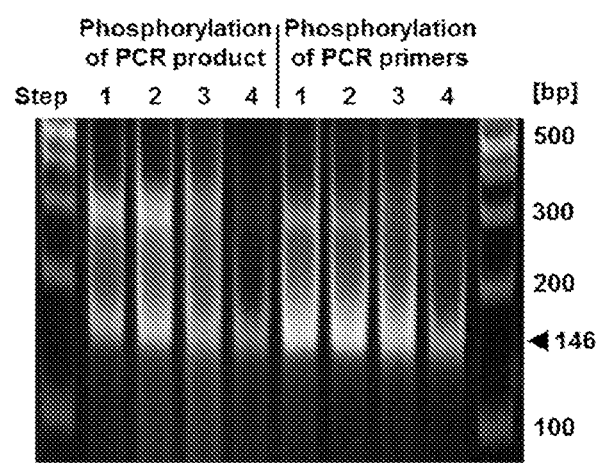

FIG. 11. Dumbbell vector generation. Generation of 146 bp dumbbell vector DNA by 5' phosphorylation of the PCR product (left side) or alternatively by using 5' phosphorylated primers for the PCR reaction (right side). Steps are referring to Steps 1 to 4 defined in FIG. 1.

Figure 12:
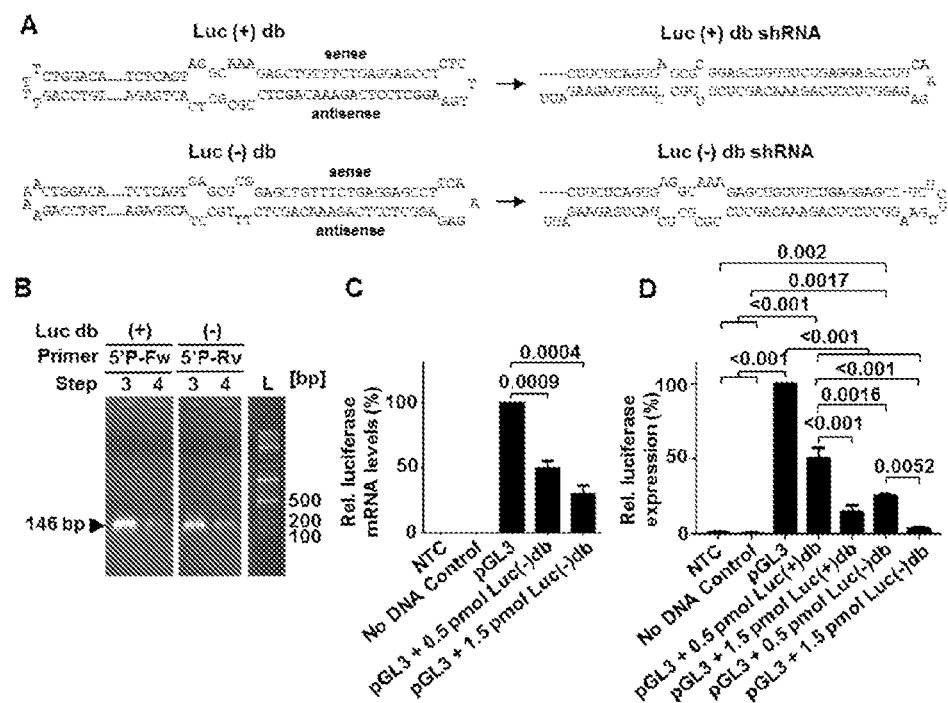

FIG. 12. Knock-down of lamin A/C in HEK 293T cells by plus (+) and minus (−) strand-derived lamin-targeting (Lam) dumbbell (db) vectors monitored using intracellular FACS. (A) Sequences and structures of dumbbell vectors and transcribed lamin A/C-targeting shRNAs. shRNA secondary structures were drawn according to predictions by mfold and RNAfold. (B-D) Representative histogram overlays of one experiment. (B) Stained (primary anti-lamin A+C antibody plus secondary donkey anti-rabbit IgG H&L) vs. unstained (primary anti-lamin A+C antibody only) non-transfected live cells. (C) Knockdown triggered by 0.1, 0.5 or 2.5 pmol plus strand-derived anti-lamin A/C shRNA expressing db vectors [Lam(+)db] or 3 pmol anti-lamin NC positive control siRNA (Lam-siRNA). (D) Knockdown triggered by 0.1, 0.5 or 2.5 pmol minus strand-derived anti-lamin NC shRNA expressing db vectors [Lam(−)db] or 3 pmol Lam-siRNA. (E-G) Knock-down of lamin NC in stained HEK293T cells relative to the non-transfected cells (100%) represented by the fraction of lamin NC-stained cells (E), the geometric mean fluorescence intensity (gMFI) of lamin NC-stained cells (F), and the median fluorescence intensity of lamin NC-stained cells (G). The control dumbbell (control db) was a 1:1 mix of plus and minus strand-derived luciferase targeting dumbbell DNA. Values are mean values±SEM of three independent experiments. The statistical analysis was performed using Student's t-test. P values indicate significance relative to the stained no transfection control. (B-G) NTC: No transfection control; No DNA control: Buffer transfected cells.

Figure 13:
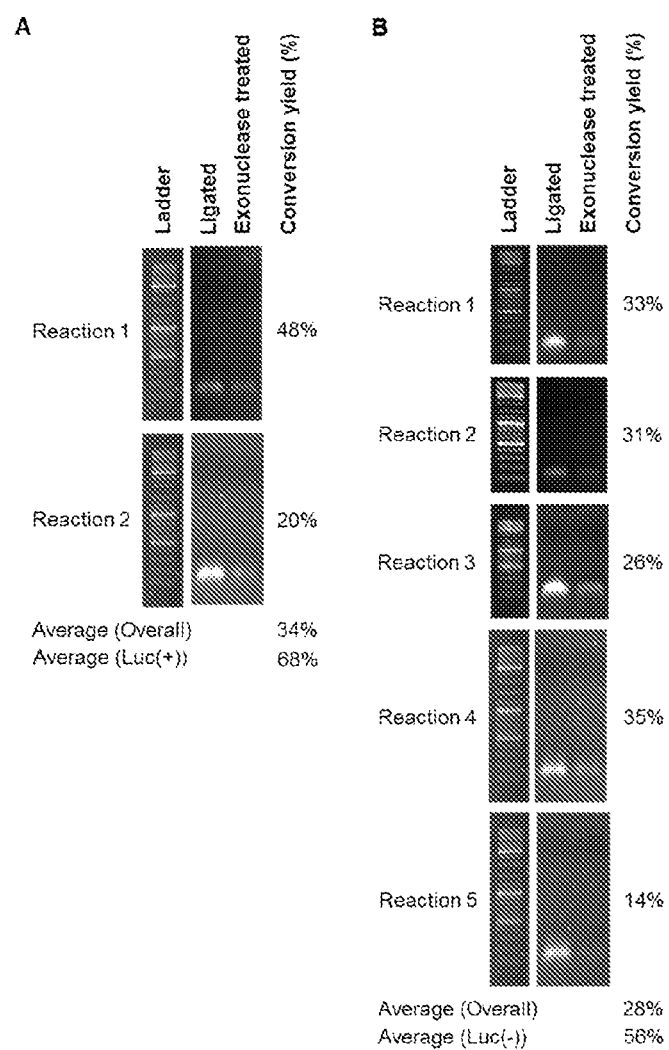

FIG. 13. Determination of conversion yields for the plus (A) and minus (B) strand-derived luciferase-targeting dumbbells. PCR was performed using a non-phosphorylated forward and a 5'-phosphorylated reverse primer. 6 □g PCR products were denatured, refolded, and ligated in 50 □l reaction volume using 100 U CircLigase. Ligated refolded dumbbell DNA was treated with exonuclease and directly comparable samples before and after exonuclease were analysed using 1% agarose gel electrophoresis. Only successfully ligated covalently closed dumbbell DNA resists exonuclease treatment. Yields of converting non-ligated into ligated overall dumbbell DNA where determined by quantifying band intensities using the software ImageJ v1.48. Since either only the plus or the minus strand-derived dumbbell DNA, i.e. only 50% of the total DNA, can theoretically be ligated in each reaction, the actual conversion yield of plus or minus strand-derived dumbbell DNA is twice as high as the detected overall conversion yield.

Figure 14:
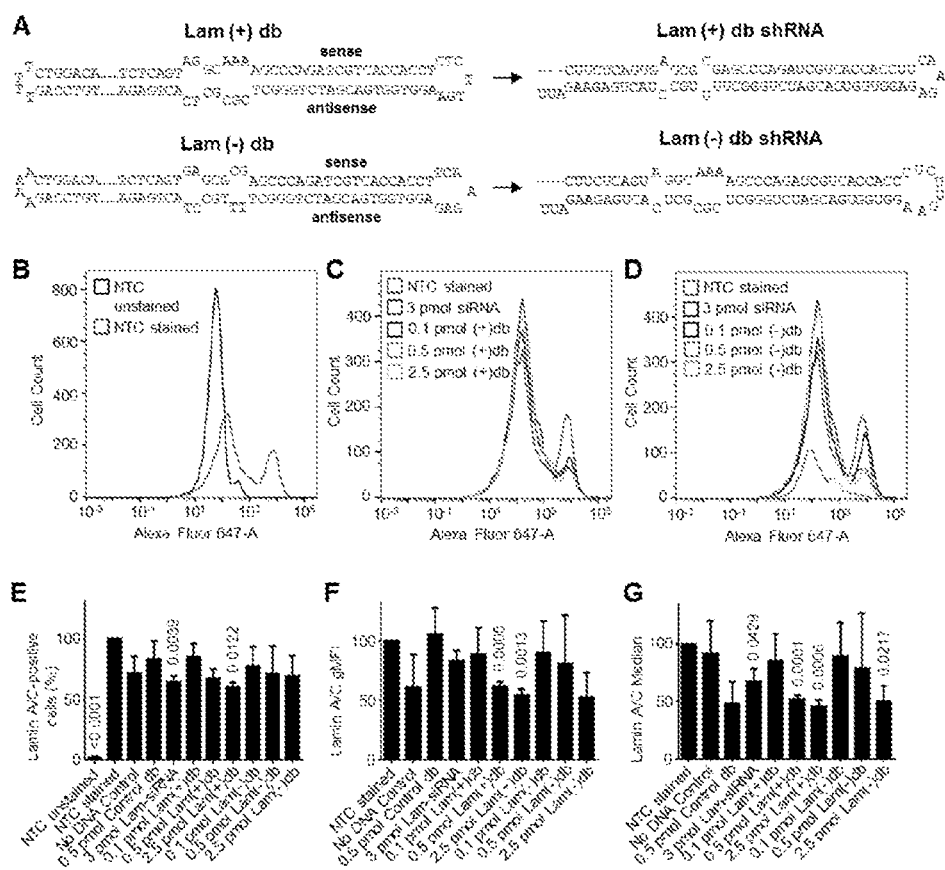

FIG. 14. Knock-down of firefly luciferase in HEK293T cells by plus (+) and minus (−) strand-derived luciferase-targeting (Luc) dumbbell (db) vectors. (A) Sequences and structures of dumbbell vectors and transcribed luciferase-targeting shRNAs. shRNA secondary structures were drawn according to predictions by mfold and RNAfold. (B) Selective generation of (+) or (−) strand-derived db vectors using either phosphorylated forward (5'P-Fw) or reverse (5'P-Rv) primers. Steps refer to Steps 1 to 4 defined in FIG. 1. (C,D) Functional validation of plus (+) and/or minus (−) strand-derived luciferase targeting db vectors. Cells were co-transfected with firefly luciferase reporter vector pGL3 and 0.5 or 1.5 pmol dumbbell vector DNA. NTC: no transfection control. Firefly luciferase mRNA (C) or expression (D) levels relative to the uninhibited negative control were measured 48 h post transfection using RT-qPCR or luciferase reporter assays. Relative RNA levels were calculated in terms of fold change ($2^{-\Delta\Delta Ct}$) where $\Delta Ct = C_{t\ luciferase} - C_{t\ \beta\text{-}Actin}$. Values are mean values±SEM of three independent experiments. The statistical analysis was performed using Student's t-test (C) or repeated one-way ANOVA with Tukey's post hoc multiple comparison test (D).

Figure 15:
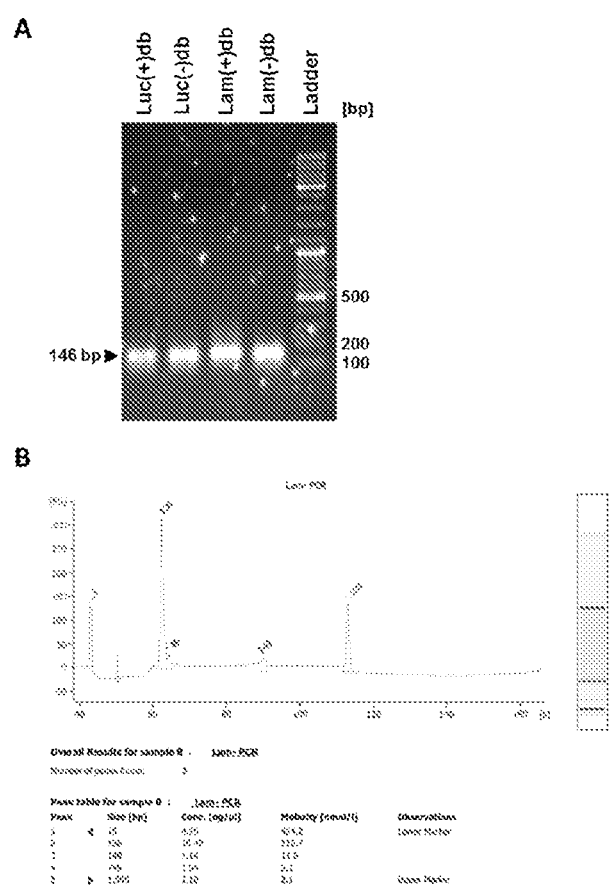

FIG. 15. Purity control of dumbbell vectors after exonuclease treatment. (A), 1% agarose gel electrophoresis of plus (+) and minus (−) strand-derived luciferase (Luc) and lamin A/C (Lam)-targeting dumbbell (db) vectors. (B), Capillary gel electrophoresis (Bioanalyzer, Agilent) of Lam(−)db DNA. The identified 136 bp peak refers to the 146 bp dumbbell vector DNA. The difference in detected and expected vector size refers to the fact that the gel retardation of dumbbell vector DNA slightly differs from that of double-stranded DNA fragments of the DNA ladder marker.

Figure 16:
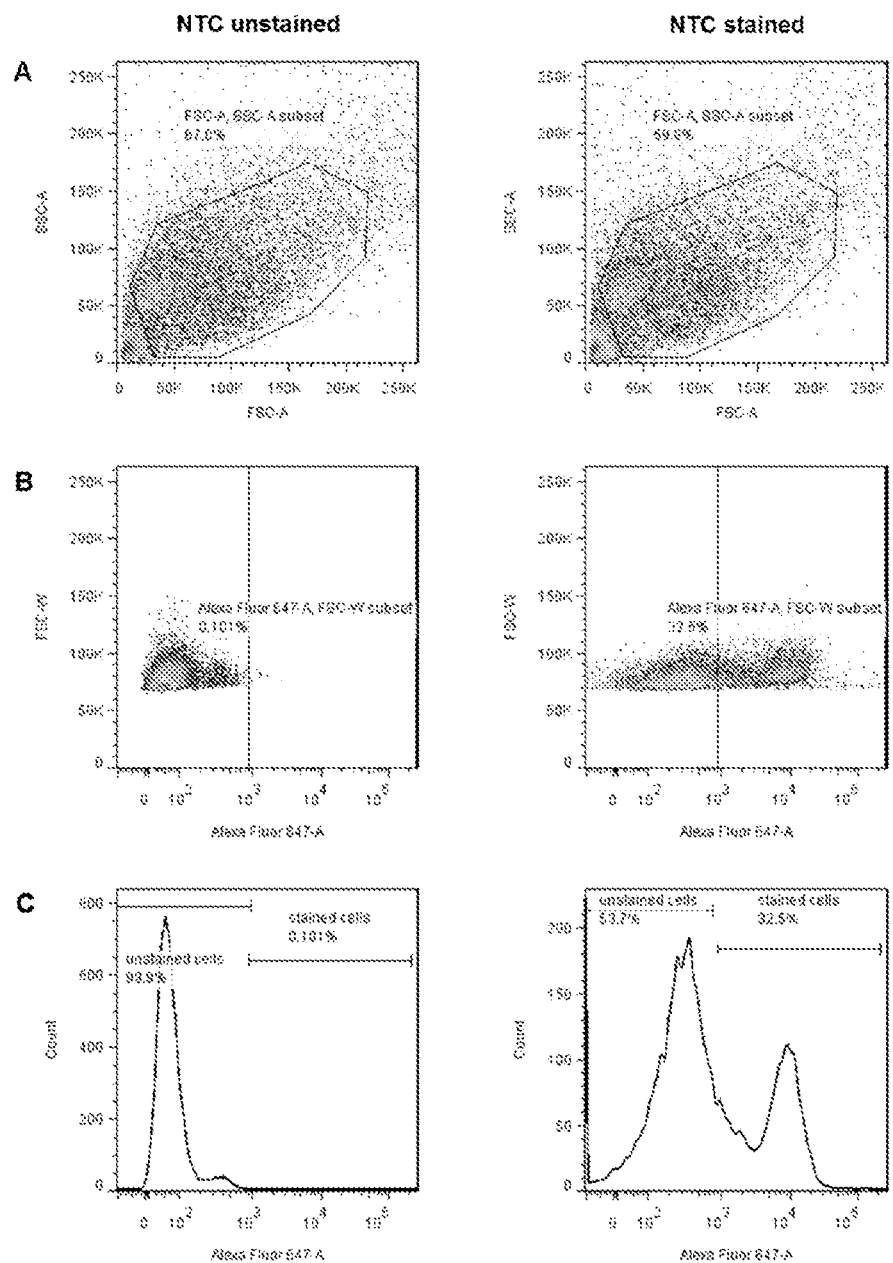

FIG. 16. Monitoring lamin A/C expression by intracellular fluorescence-activated cell sorting (FACS). Cellular lamin A/C expression n non-transfected cells (NTC) was labelled by anti-lamin A+C primary antibody (left panels: unstained) and then stained with donkey anti-rabbit IgG H&L Alexa Fluor 647-A secondary antibody (right panels: stained). Gating of live HEK293T cells (A), Alexa Fluor 647-A scatter plots (B), and histograms (C).

Sequence Listing
SEQ ID NO 1:
5'-
AGCTTCGCGCTCACTGAGAAGATTTTTCTGTGCTCTCATACAGAACTTATA
AGATTCCCAAATCCAAAGACATTTCACGTTTATGGTGATTTCCCAGAACAC
ATAGCGACATGCAAATATGAATTGTCCAGTT-3'

SEQ ID NO 2:
5'P-
GGACAATTCATATTTGCATGTCGCTATGTGTTCTGGGAAATCACCATAAAC
GTGAAATGTCTTTGGATTTGGGAATCTTATAAGTTCTGTATGAGAGCACAG
AAAAATCTTCTCAGTGAGCGCGA-3'

SEQ ID NO 3:
5'P-
TTCTGGACAATTCATATTTGCATGTCGCTATGTGTTCTGGGAAATCACCAT
AAACGTGAAATGTCTTTGGATTTGGGAATCTTATAAGTTCTGTATGAGAGC
ACAGAAAAATCTTCTCAGTAGGCAAAG-3'

SEQ ID NO 4:
5'-
GATCCTTTGCCTACTGAGAAGATTTTTCTGTGCTCTCATACAGAACTTATA
AGATTCCCAAATCCAAAGACATTTCACGTTTATGGTGATTTCCCAGAACAC
ATAGCGACATGCAAATATGAATTGTCCAGAAAACT-3'

SEQ ID NO 5:
5'-tgaaggctcctcagaaacagctcCGCGCTCACTGAGAAGATTT-3'

SEQ ID NO 6:
5'-tgaaagcccagatcgtcaccacccgcCGCGCTCACTGAGAAGATTT-3'

SEQ ID NO 7:
5'-agagaggctcctcagaaacagctcTTTGCCTACTGAGAAGATTTTTCTGT-3'

SEQ ID NO 8:
5'-agagaagcccagatcgtcaccaccttTTTGCCTACTGAGAAGATTTTTCTGT-3'

SEQ ID NO 9:
5'-
GGACAATTCATATTTGCATGTCGCTATGTGTTCTGGGAAATCACCATAAAC
GTGAAATGTCTTTGGATTTGGGAATCTTATAAGTTCTGTATGAGAGCACAG
AAAAATCTTCTCAGTGAGCGCGA-3'

SEQ ID NO 10:
5'-

-continued

TTCTGGACAATTCATATTTGCATGTCGCTATGTGTTCTGGGAAATCACCAT

AAACGTGAAATGTCTTTGGATTTGGGAATCTTATAAGTTCTGTATGAGAGC

ACAGAAAAATCTTCTCAGTAGGCAAAG-3'

SEQ ID NO 11:
5'-CGCTGGGCGTTAATCAAAGA-3'

SEQ ID NO 12:
5'-CTGGCACCCAGCACAATG-3'

SEQ ID NO 13:
5'-GTGTTCGTCTTCGTCCCAGT-3'

SEQ ID NO 14:
5'-GCCGATCCACACGGAGTACT-3'

SEQ ID NO 15:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTAGGCAAAGAGCTGTTTCTGAGGAGCCTCTC

TTGAAGGCTCCTCAGAAACAGCTCGCGGCTCACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

SEQ ID NO 16:
5'-
CUUCUCAGUGAGCGCGGAGCUGUUUCUGAGGAGCCUUCAAGAGAGGCUCCU

CAGAAACAGCUCUUUGCCUACUGAGAAGAUU-3'

SEQ ID NO 17:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTGAGCGCGGAGCTGTTTCTGAGGAGCCTTCA

AGAGAGGCTCCTCAGAAACAGCTCTTTGCCTACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

SEQ ID NO 18:
5'-
CUUCUCAGUGAGGCAAAGAGCUGUUUCUGAGGAGCCUCUCUUGAAGGCUCC

UCAGAAACAGCUCCGCGCUCUACUGAGAAGAUU-3'

SEQ ID NO 19:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTAGGCAAAAGCCCAGATCGTCACCACCTCTC

TTGAAGGTGGTGACGATCTGGGCTCGCGCTCACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

SEQ ID NO 20:
5'-
CUUCUCAGUGAGCGCGAGCCCAGAUCGUCACCACCUUCAAGAGAGGUGGUG

ACGAUCUGGGCUUUUGCCUACUGAGAAGAUU-3'

SEQ ID NO 21:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTGAGCGCGAGCCCAGATCGTCACCACCTTCA

AGAGAGGTGGTGACGATCTGGGCTTTTGCCTACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

SEQ ID NO 22:
5'-
CUUCUCAGUGAGGCAAAAGCCCAGAUCGUCACCACCCUCUUGAAGGUGGUG

ACGAUCUGGGCUCGCGCUCACUGAGAAGAUU-3'

SEQ ID NO 23:
5'-
CGCGCTCACTGAGAAGATTTTTCTGTGCTCTCATACAGAACTTATAAGATT

CCCAAATCCAAAGACATTTCACGTTTATGGTGATTTCCCAGAACACATAGC

GACATGCAAATATGAATTGTCCAGTTTTCTGGACAATTCATATTTGCATGT

CGCTATGTGTTCTGGGAAATCACCATAAACGTGAAATGTCTTTGGATTTGG

GAATCTTATAAGTTCTGTATGAGAGCACAG**AAAAATCTTCTCAGTAGGCAA
A**-3'

SEQ ID NO 24:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTAGGCAAAGAGCTGTTTCTGAGGAGCCTCTC

TTGAAGGCTCCTCAGAAACAGCTCGCGGCTCACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

SEQ ID NO 25:
5'-
TTTTCTGGACAATTCATATTTGCATGTCGCTATGTGTTCTGGGAAATCACC

ATAAACGTGAAATGTCTTTGGATTTGGGAATCTTATAAGTTCTGTATGAGA

GCACAGAAAAATCTTCTCAGTGAGCGCGGAGCTGTTTCTGAGGAGCCTTCA

AGAGAGGCTCCTCAGAAACAGCTCTTTGCCTACTGAGAAGATTTTTCTGTG

CTCTCATACAGAACTTATAAGATTCCCAAATCCAAAGACATTTCACGTTTA

TGGTGATTTCCCAGAACACATAGCGACATGCAAATATGAATTGTCCAG-3'

Materials & Methods

Oligodeoxyribonucleotides (ODNs) and primers Universal Template. Due to internal self-complementarity, the universal template could not be generated by gene synthesis and instead was assembled from two pairs of complementary oligodeoxyribonucleotides (IDT, Skokie, IL) (FIG. S1A,B): Oligo UT1: 5'-AGCTTCGCGCTCACTGAGAAGATTTTTCTGTGCTCTCATACAGAACTTATAAGATTCCCA AATCCAAAGACATTTCACGTTTATGGTGAT- TTCCCAGAACACATAGCGACATGCAAATATGAATTGTCCAGTT-3'; Oligo UT2: 5'-P-GGACAATTCATATTTGCATGTCGCTATGTGTTCTGGGAAATCACCATAAACGTGAAATGT CTTTGGATTTGGGAATCTTATAAGTTCTGTATGAGAGCACAGAAAAATCTTCTCAGTGAG CGCGA-3'; Oligo UT3: 5'-P-TTCTGGACAATTCATATTTGCATGTCGCTATGTGTTCTGGGAAATCACCATAAACGTGAA ATGTCTTTGGATTTGGGAATCTTATAAGTTCTGTATGAGAGCACAGAAAAA TCTTCTCAGT AGGCAAAG-3'; Oligo UT4: 5'-GATCCTTTGCCTACTGAGAAGATTTTTCTGTGCTCTCATACAGAACTTATAAGATTCC-CAA ATCCAAAGACATTTCACGTTTATGGTGATTCCCAGAACACATAGCGACATGCAAATATG AATTGTCCAGAAAACT-3'. Bold: HindIII and BamHI compatible overhangs; underlined: dumbbell loop-forming tetranucleotide. The 5' phosphorylated oligos UT2 and UT3 were hybridized with the complementary oligos UT1 and UT4, respectively. The resulting UT1/UT2 and UT3/UT4 duplexes were ligated to form the universal template sequence bearing HindIII and BamHI-compatible 5'-overhangs which was subsequently cloned into pVax1 (Thermo Fisher Scientific, Waltham, MA) yielding the universal template vector pVax1-UT (FIG. S1B). For cloning we used the recA-deficient E. coli strain Top10. Cloning of the universal template was confirmed by PCR and by FastDigest BamHI/HindIII (Thermo Fisher Scientific, Waltham, MA) endonucleolytic cleavage followed by analytical agarose gel electrophoresis which yielded the expected insert size of 262 bp and by sequencing of the ligation sites (FIG. S1C,D). Sequencing of the complete universal template was unsuccessful due to the high degree of self-complementarity.

Primers for the production of firefly luciferase- or lamin A/C-targeting shRNA expressing dumbbells. Luciferase- or lamin NC-specific primers were synthesized by AITbiotech (Singapore) or IDT (Singapore). Upper case letters indicate the universal template binding sites and lower case letters indicate the shRNA coding sequences in which the loop-forming nucleotides are underlined: Forward primers: FP_Luciferase 5'-tgaaggctcctcagaaacagctcCGCGCTCACTGAGAAGATTT-3'; FP_Lamin 5'-tgaaagcccagatcgtcaccacccgcCGCGCTCACTGAGAAGATTT-3'. Reverse primers: RP_Luciferase 5'-agagaggctcctcagaaacagctcTTTGCCTACTGAGAAGATTTTTCTGT-3'. RP_Lamin 5'-agagaagcccagatcgtcaccaccttTTTGCCTACTGAGAAGATTTTTCTGT-3'. Blocking ODNs: Two blocking ODNs (IDT, Skokie, IL) were added to the PCR to suppress refolding and self-priming of the universal template strands. Block_1:

5'-
GGACAATTCATATTTGCATGTCGCTATGTGTTCTGGGAAATCACCATAAAC

GTGAAATGTCTTTGGATTTGGGAATCTTATAAGTTCTGTATGAGAGCACAG

AAAAATCTTCTCAGTGAGCGCGA-3'; Block_2:

5'-

TTCTGGACAATTCATATTTGCATGTCGCTATGTGTTCTGGGAAATCACCAT

AAACGTGAAATGTCTTTGGATTTGGGAATCTTATAAGTTCTGTATGAGAGC

ACAGAAAAATCTTCTCAGTAGGCAAAG-3'.

Primers for quantitative reverse transcription PCR (RT-qPCR). Primers for the quantification of luciferase and β-actin mRNA levels were synthesized by AITbiotech (Singapore). PCR forward primers: qPCR_FP_Luciferase 5'-CGCTGGGCGTTAATCAAAGA-3'; qPCR_RP_β-actin 5'-CTGGCACCCAGCACAATG-3'. Reverse transcription and PCR reverse primers: qPCR_RP_Luciferase 5'-GTGTTCGTCTTCGTCCCAGT-3'; qPCR_RP_β-actin 5'-GCCGATCCACACGGAGTACT-3'.

Primer phosphorylation. For the generation of strand-specific dumbbell vectors, either the forward or the reverse primers were 5'-phosphorylated. Each 50 pmol primer were incubated with 10 U T4 polynucleotide kinase (Thermo Fisher Scientific, Waltham, MA) in the presence of 1 mM ATP at 37° C. for 20 mins followed by heat inactivation of the enzyme at 75° C. for 10 mins.

Dumbbell Vector Generation

PCR amplification of dumbbell vector DNA. PCR amplification of the universal template and appendage of shRNA encoding DNA was carried out using 1 U Taq DNA Polymerase (Invitrogen), 1.0 µM of each primer and blocking ODNs, 0.2 mM of each dNTP (Invitrogen), 100 ng of HindIII/BamHI cleaved pVax1-UT, 5% v/v DMSO (Thermo Fisher Scientific, Waltham, MA) in a reaction volume of 30-50 µl in 1× Taq DNA Polymerase buffer (Invitrogen). Linearisation of pVax1-UT usually improves the PCR yields but is not essential. Thermal cycling was carried out as follows: Initial denaturation at 96° C. for 5 mins; 27 cycles of denaturation (95° C., 30 sec), annealing (59° C., 30 sec), and extension (72° C., 1 min); and final extension at 72° C. for 10 mins. A 50 µl PCR reaction yielded about 10 µg DNA.

Strand separation and annealing. PCR products were purified through silica-membrane based spin columns (QIAquick PCR purification kit, Qiagen, Hilden, Germany). Purified products were diluted to 400 µl in 1× hybridisation buffer (1 M NaCl, 100 mM MgCl$_2$, and 200 mM Tris-HCl, pH 7.4), heat-denatured at 96° C. for 5 mins followed by gradual cooling to room temperature to allow for intramolecular folding of plus and/or minus strand dumbbell vectors. The resulting DNA was concentrated using ethanol precipitation, pelleted by centrifugation, and resuspended in nuclease-free water.

Ligation of single-stranded loop DNA. 1 to 6 µg (~10 to 60 pmol) of DNA was incubated with 2.5 mM MnCl$_2$, 1 M Betaine (Sigma, St. Louis, MO) and 50 to 100 U CircLigaseII (Epicenter, Madison, WI) in 1× CircLigaseII reaction buffer at 60° C. for 16 hours, followed by heat inactivation of the ligase at 80° C. for 10 mins. Highest conversion yields were observed when ligating 6 µg DNA with 100 U CircLigase.

Exonuclease treatment. After ligation, products were treated with 10 U of T7 DNA polymerase (Thermo Fisher Scientific, Waltham, MA) at 37° C. for 1 h followed by heat inactivation at 80° C. for 10 mins. Products were assessed on 10% native polyacrylamide gels or 1% agarose gels, stained with ethidium bromide post electrophoresis and/or purified using phenol-chloroform-isoamylalcohol (25:24:1) extraction (1×), chloform-isoamylalcohol (24:1) re-extraction (3×), and ethanol precipitation.

Target Gene Knockdown Assays

Luciferase knockdown assays. HEK293T cells were maintained in Dulbecco's Modified Eagle's Medium (Hyclone, South Logan, UT) supplemented with 10% (v/v) fetal bovine serum (Hyclone, South Logan, UT) and 1% penicillin-streptomycin antibiotic solution (Thermo Fisher Scientific, Waltham, MA). 24 hours prior to transfection, $2\times10^4$ cells/well were seeded in a 96-well plate. Cells were co-transfected with 100 ng of luciferase expression plasmid pGL3 (Promega, Madison, WI) and 1.5 pmol or 0.5 pmol of either plus- or minus-strand dumbbell vector DNA using Lipofectamin 2000 (Thermo Fisher Scientific, Waltham, MA) and a reagent:DNA ratio of 1:2.5. For the positive control (pGL3 only) empty pVax1 (Thermo Fisher Scientific, Waltham, MA) was used as feeder DNA to ensure all cells received the same quantity of DNA. 48 hours post transfection, cells were washed with sterile PBS and lysed in 20 µl passive lysis buffer (Promega, Madison, WI) for 20 mins employing gentle shaking. 10 µl of lysate was treated with 50 µl of LARII reagent (Promega, Madison, WI) and luminescence was quantified on the Biotek Reader (Biotek Instruments, Winooski, VT).

Monitoring lamin A/C knockdown by intracellular fluorescence-activated cell sorting (FACS). HEK293T cells were cultivated and seeded in 96-well plates 24 hours prior to transfection as described above. Cells were transfected with 0.1, 0.5 or 2.5 pmol dumbbell vector DNA or 3 pmol siGENOMELamin A/C control siRNA (Dharmacon, Lafayette, CO) using Lipofectamine 3000 (Thermo Fisher Scientific, Waltham, MA) according to the manufacturer's protocol, Medium was changed 24 hours post transfection and cells were harvested after 48 hours. For FACS analyses, the media was aspirated and the cells were rinsed once with PBS before trypsinisation with 50 µl of 1× trypsin-EDTA (Gibco), Trypsinised cells were collected by centrifugation at 4200 rpm for 6 min in 200 µl media. Pelleted cells were resuspended in 100 µL media, fixed and permeabilized with Intracellular Fixation and Permeabilization Buffer Set (eBioscience, San Diego, CA) according to manufacturer's protocol prior to intracellular staining. To assess lamin A/C knockdown, cellular lamin A/C was stained by anti-lamin A+C antibody (ab133256) (1/200) and donkey anti-rabbit IgG AF647 (ab150075) (1/200) (Abcam, Cambridge, UK), FACS was performed on LSRFortessa cell analyser, and FACSDiva software v6.1.3 (BD Biosciences, San Jose, CA) was used for the acquisition of the samples. Flow Jo software V10.5.2 (Tree Star, Ashland, OR) was used for data analyses.

Computational Secondary Structure Prediction

Minimum free energy secondary structures of DNA and RNA were folded using the algorithms mfold and/or RNAfold.[17,18]

Statistical Analysis

Diagrams represent mean values±SEM of three independent experiments. The statistical analysis was performed using repeated one-way ANOVA with Tukey's post hoc multiple comparison's test (luciferase knock-down data) or using Student's t-test (lamin NC knock-down data). The GraphPad Prism version 7 software (GraphPad, La Jolla, CA) was used for the statistical analysis. P values are as indicated.

Example

Universal Template-Assisted, Cloning- and Endonuclease-Free Method for the Generation of Dumbbell-Shaped Vectors In current state-of-the-art protocols, the generation of every new dumbbell vector starts with individual cloning the sequence of interest to be implemented into the dumbbell into a plasmid vector. The method of this invention requires to prepare only one universal template, comprising regulatory sequences such as promoter, enhancer, DNA nuclear localisation signal, intron, transcriptional terminator, RNA nuclear export signal, WPRE or others. The sequences of interest are then introduced via chemically synthesised PCR primers and no further cloning and no endonucleases are required (FIGS. 1-7). Such generated dumbbells can function as molecular decoys or expression vectors. The expression vectors can express non-coding RNA including shRNA, pre-miRNA, miRNA, aptamers, antisense RNA, and antisense miRNA (FIGS. 1-4, 6, 7) and/or express peptide or protein coding RNA (FIGS. 5-7). The expression cassettes for hairpin-structured RNA such as shRNA and pre-miRNA can be designed as hairpin template-transcribing expression cassettes in which the expression cassette resembles the hairpin structure of the transcribed RNA. In these vectors, redundant sequences are eliminated and transcription goes around one of the dumbbell loops. The hairpin template-transcribing dumbbell vectors can be generated using the method of this invention (FIGS. 1-5).

The new method is based on PCR amplification of a universal DNA template which, for shRNA expression, comprises an inverted repeat of (i) the minimal H1 promoter,[15] (ii) a polymerase III transcriptional terminator ($T_5$), and (iii) the hsa-miR-30 precursor stem (FIG. 8A). The hsa-mir-30 stem was reported to facilitate shRNA processing and has been successfully implemented in dumbbell vector design.[13,16] Once generated, the universal template can be used for cloning-free generation of any shRNA expressing dumbbell vectors. Sequences coding for the expression of the respective small RNA are introduced during the PCR by the PCR primers (Step 1). Irrespective of the small RNA-specific 5' portion of the PCR primers, they all harbour the same 3' terminal target binding sites which facilitates parallelised PCR amplifications. Both strands of the universal DNA template have a high degree of self-complementarity and to improve its amplification, blocking oligos are added to the PCR reaction to suppress intramolecular refolding of the denatured DNA and to support primer binding. Each of the two DNA strands (+ and −) of the resulting double-stranded PCR product yields, after dilution, heat denaturation and intramolecular refolding, an open dumbbell scaffold with dangling 5' and 3' ends (Step 2). These ends are then ligated using a single-stranded DNA (ssDNA) ligase (Step 3). All DNA molecules harbouring 5' or 3' ends are removed by exonuclease digestion yielding clean, covalently closed dumbbell vectors (Step 4). With the decision of using either one or two 5'-phosphorylated PCR primers, the plus strand, the minus strand or both strands will produce dumbbell vectors.

Generation of the universal template was challenging due to the high degree of self-complementarity and all attempts to generate the universal template by gene synthesis failed. Instead the universal template was assembled from two pairs of complementary oligodeoxyribonucleotides (oligos) in which the self-complementary sequence portions were separated from each other (FIG. 8A-C). Pairs of complementary oligos were annealed each forming one complementary 3'-overhang and either a HindIII or BamHI 5'-overhang. Pairs of annealed oligos were then first ligated using the adhesive 3' ends, gel purified, and inserted into the cloning vector pVax1 using the HindIII and BamHI cloning sites yielding the universal template vector pVax1-UT. Successful cloning of the universal template was proven by analytical restriction endonuclease cleavage and subsequent gel electrophoresis of the fragments as well as by sequencing: The HindIII/BamHI double digestion yielded the expected insert size of 262 bp; sequencing of the complete insert was unsuccessful due to insert self-complementarity but the cloning sites could be sequenced (FIG. 8D,E).

Next we aimed to PCR-amplify the universal template using primers that introduced the sequence coding for a published firefly luciferase-targeting shRNA.[9] However, intrinsic self-complementarity of the universal template was impeding conventional PCR amplification which didn't yield any product of the expected size. Products were observed after adding two long blocking oligos into the PCR reaction (FIG. 9A). These blocking oligos were designed such that they were complementary to the respective 5' half of the plus or the minus strand of the universal template, thus suppressing intramolecular strand refolding and facilitating primer binding to the 3' ends of the template DNA (FIG. 2). Because the blocking oligos bind to the universal template sequence, they represent a constant, target- and shRNA-independent component of this dumbbell generation protocol. The obtained PCR products corresponded in size with the double-stranded universal temple (303 bp) and the refolded single strands (146 bp). Addition of 5% (v/v) DMSO into the PCR reaction yielded more of the larger product, indicating a more efficient amplification as primer binding and extension competed more successfully with single-strand refolding (FIG. 9B). Heat denaturation and refolding of the purified PCR products then yielded more of the hairpin structured single-strands (FIG. 9C, lanes 2). As expected, the ssDNA ligation (lanes 3) and subsequent exonuclease digestion (lanes 4) yielded exonuclease-resistant dumbbell vector DNA only if 5'-phorsphorylated primers were used for the PCR (FIG. 9C).

With the decision to use either a 5'-phosphorylated forward primer, a 5'-phoshphorylated reverse primer or two phosphorylated primers for PCR, only (i) plus strand-derived dumbbells, or (ii) minus strand-derived dumbbells, or (iii) a mix of both can be generated (FIGS. 2 and 10). In order to obtain a mix of plus and minus strand-derived dumbbells, it doesn't make a difference if the 5' ends of the PCR primers or alternatively of the PCR product are phosphorylated (FIG. 11). In this example, plus and minus strand-derived dumbbells and the expressed shRNAs are very similar but not identical as they differ with regard to sequence and structure in the loops and in the hsa-miR-30 stem (FIGS. 12A and 10). The asymmetry in the mi RNA stem region is owed to the fact that correct transcription of a partly mismatched miRNA precursor RNA can only be achieved if the hairpin template-transcribing dumbbell harbours corresponding mismatches as well. Consequently, only the plus strand-derived dumbbell expresses the shRNA extended with the original miR-30 stem (FIG. 12A). The shRNA expressed from the minus strand-derived dumbbell is extended with a miR-like stem formed by the antisense sequences of miR-30 and carries a loop that represents the reverse complement of the loop in the plus strand-derived shRNA. The observed conversion yield, i.e. the fraction of refolded 146 bp dumbbell vector DNA that was successfully ligated and resisted subsequent exonuclease treatment, was measured to be 34% or 28% for the production of the plus or minus strand-derived luciferase-targeting dumbbells (FIG. 13). Considering, that only one PCR primer was phosphorylated for the generation of these dumbbells and that consequently only half of the refolded DNA could theoretically be ligated, then the actual conversion yield of ligatable plus or minus strand-derived dumbbell DNA is 68% or 56%. In these reactions we ligated 6 µg of DNA using 100 U of CircLigase.

Employing the above protocol using either phosphorylated forward or reverse primers, we generated both plus and minus strand-derived luciferase- or lamin NC-targeting dumbbells in separate reactions (FIGS. 12 and 14). The purity of the vectors after exonuclease treatment was controlled using agarose gel electrophoresis (FIG. 15A). Additional capillary gel electrophoresis determined the purity of the minus strand-derived lamin NC-targeting dumbbell to be 83% (FIG. 15B). To measure dumbbell vector-triggered luciferase knockdown, HEK293T cells were co-transfected with the luciferase expression vector pGL3-Control and 0.5 or 1.5 pmol of plus or minus strand-derived dumbbell vector DNA using Lipofectamine 2000. 48 hours post transfection, firefly luciferase mRNA and activity levels were quantified relative to the pGL3-Control vector (FIG. 12C,D). Both dumbbells triggered a significant, dose-dependent luciferase knockdown which surprisingly was more pronounced in case of the minus strand-derived dumbbell vector indicating the non-natural miR-like stem was functional. The knockdown triggered by the plus strand-derived dumbbell was 85% (p<0.001) or 50% (p<0.001) at 1.5 or 0.5 pmol vector DNA, and the minus strand-derived dumbbell triggered 97% (p<0.001) or 75% (p<0.001) knockdown at 1.5 or 0.5 pmol DNA, respectively relative to the pGL3 positive control. To investigate the knockdown of lamin NC, HEK293T cells were transfected with 0.1, 0.5 or 2.5 pmol of plus or minus strand-derived dumbbell vector DNA or alternatively with 3 pmol siGENOMELamin A/C positive control siRNA or 0.5 pmol luciferase-targeting dumbbell control vector DNA (1:1 mix of plus and minus strand-derived dumbbells) using Lipofectamine 3000. 48 hours post transfection, intra-cellular lamin NC was stained using rabbit anti-lamin A+C primary antibody and donkey anti-rabbit IgG H&L AF647 secondary antibody, and lamin A/C knock-down was monitored by flow cytometry analyses (FIGS. 14,16). While the plus strand-derived dumbbell triggered a significant, dose-dependent lamin A/C knock-down at 2.5 or 0.5 pmol DNA, the knock-down observed with the minus strand-derived dumbbell was less pronounced.

The protocol described here combines all the advantages of previously reported protocols for dumbbell vector production. It represents (i) a cloning-free protocol which (ii) does not involve any restriction or nicking endonucleases, it (iii) employs an efficient intra-molecular ligation reaction, and it (iv) allows production of extremely small hairpin template-transcribing dumbbell vectors. The previously described gap-primer PCR protocol also involves an intra-molecular ligation but requires a cloning step for the generation of every new vector and it is not suitable to generate hairpin template-transcribing vectors due to the presence of abasic sequence positions.[14] Conversely, the method described by Jiang et al. is suitable to produce hairpin template-transcribing dumbbells but requires restriction and nicking endonucleases and involves a less efficient inter-molecular ligation reaction.[9,13] The PCR primers used for the protocol reported here always harbour the same 3' terminal template binding sites as well as a 5' terminal sequence that depends on and changes with the respective small RNA but which is to a great extent identical within each respective primer pair. Hence, the primer annealing temperatures are always the same and primer dimer formation can widely be excluded which both facilitates parallelised PCR reactions using a single cycling programme. The subsequent ligation reaction represents an intramolecular ligation which is generally more efficient compared with alternative protocols involving intermolecular loop ligation. As a corollary, the conversion yields observed for this method are higher than those reported for protocols employing inter-molecular ligation reactions. For the gap-primer PCR method, higher conversion yields of up to 92% were observed when ligating double-stranded nicked dumbbell DNA using the T4 DNA ligase; however, only slightly higher conversion yields of 75% were observed with the gap-primer PCR method when ligating dangling single-stranded 5' ends with base-paired 3' ends using the CircLigase. The purity of dumbbell DNA produced with the method described here was within the purity range of 82% to 94% of vectors produced with the gap-primer PCR method. Additional purification steps will be required for future pre-clinical and clinical applications.

We demonstrate the proof-of-principle that this new method can generate partly mismatched shRNA-expressing dumbbell vectors indicating the technology might also be explored for the generation of miRNA-expressing dumbbells. Mismatches in dumbbell vectors were reported earlier and demonstrated not to impair vector activity.[13] On the contrary, terminal single-nucleotide mismatches were found to improve nuclear targeting and activity of dumbbell-shaped expression vectors.[14]

We observed that among the luciferase- or lamin NC-targeting dumbbells, the minus or plus strand-derived dumbbell exhibited a stronger target gene knockdown activity, respectively. This difference might be assigned to differences with regard to the efficiency and accuracy of endogenous shRNA processing by Dicer which depends on the sequence and structure of shRNA loops and stems. Here we employed the hsa-miR-30 stem, as miRNA stems were reported to facilitate shRNA processing and knockdown activities in most of the cases.[16] Consequently, though the respective plus and minus strand-derived dumbbells code for identical guide sequences, the transcribed small hairpin RNAs comprise different microRNA stems and different loops as emphasized above. Hence, differences in Dicer processing might lead to different guide RNA levels and/or differences with regard to the exact 5' and 3' termination of guide RNA sequences. These differences can account for the observation that, depending on the targeted sequences and the corresponding guide RNA sequences and structures, either the plus or the minus strand-derived dumbbell triggers stronger target gene knockdown. However, when forgoing the inclusion of a miRNA stem and when concurrently considering palindromic loop sequences, both plus and minus strand-derived dumbbells would be identical and a single reaction would generate a single vector only.

In conclusion, this novel method efficiently generates size-minimised hairpin template-transcribing dumbbells in a short period of time and at low costs and can be explored for the parallelised production of shRNA or miRNA expression vectors for functional genomics screens or drug development.

REFERENCES

1. Biasco, L., Baricordi, C. and Aiuti, A. (2012). Retroviral Integrations in Gene Therapy Trials. Mol. Ther. 20, 709-716.
2. Yin, H., Kanasty, R. L., Eltoukhy, A. A., Vegas, A. J., Dorkin, J. R. and Anderson, D. G. (2014). Non-viral vectors for gene-based therapy. Nat. Rev. Genet. 15, 541-555.
3. Mok, P. L., Cheong, S. K., Leong, C. F., Chua, K. H. and Ainoon, O. (2012). Extended and stable gene expression via nucleofection of MIDGE construct into adult human marrow mesenchymal stromal cells. Cytotechnology. 64, 203-216.
4. Kaur, T., Slavcev, R. A. and Wettig, S. D. (2009). Addressing the Challenge: Current and Future Directions in Ovarian Cancer Therapy. Curr. Gene Ther. 9, 434-458.
5. Lopez-Fuertes, L., Perez-Jiménez, E., Vila-Coro, A. J., Sack, F., Moreno, S., Konig, S. A., et al. (2002). DNA vaccination with linear minimalistic (MIDGE) vectors confers protection against *Leishmania major* infection in mice. Vaccine. 21, 247-257.
6. Schakowski, F., Gorschlüter, M., Junghans, C., Schroff, M., Buttgereit, P., Ziske, C., et al. (2001). A Novel Minimal-Size Vector (MIDGE) Improves Transgene Expression in Colon Carcinoma Cells and Avoids Transfection of Undesired DNA. Mol. Ther. 3, 793-800.
7. Zanta, M. A., Belguise-Valladier, P. and Behr, J.-P. (1999). Gene delivery: A single nuclear localization signal peptide is sufficient to carry DNA to the cell nucleus. Proc. Natl. Acad. Sci. USA 96, 91-96.
8. Fogg, J. M., Kolmakova, N., Rees, I., Magonov, S., Hansma, H., Perona, J. J. et al. (2006). Exploring writhe in supercoiled minicircle DNA. J Phys Condens Matter 18: S145-S159.
9. Jiang, X., Yu, H., Teo, C. R., Tan, G., Goh, S. C., Patel, P., et al. (2016). Advanced design of dumbbell-shaped genetic minimal vectors improves non-coding and coding RNA expression. Mol. Ther. 24(9), 1581-1591.
10. Cost, G. J. (2007). Enzymatic ligation assisted by nucleases: simultaneous ligation and digestion promote the ordered assembly of DNA. Nat. Protoc. 2, 2198-2202.
11. Taki, M., Kato, Y., Miyagishi, M., Takagi, Y. and Taira, K. (2004). Small-Interfering-RNA Expression in Cells Based on an Efficiently Constructed Dumbbell-Shaped DNA. Angew. Chem., Int. Ed. 43, 3160-3163.
12. Taki, M., Kato, Y., Miyagishi, M., Takagi, Y., Sano, M. and Taira, K. (2003). A Direct and efficient synthesis method for dumbell-shaped linear DNA using PCR in vitro. Nucleic Acids Symp. Ser. 3, 191-192.
13. Jiang, X. and Patzel, V. (2017). Formation of Minimised Hairpin Template-transcribing Dumbbell Vectors for Small RNA Expression. Bio-Protocol. 7(11), 1-10.
14. Yu, H., Jiang, X., Hang, L., Tan, K. T. and Patzel, V. (2015). Efficient Production of Superior Dumbbell-Shaped DNA Minimal Vectors for Small Hairpin RNA Expression. Nucleic Acids Research. 43(18), e120.
15. Myslinski, E., Ame, J. C., Krol, A. and Carbon, P. (2001). An unusually compact external promoter for RNA polymerase III transcription of the human H1 RNA gene. Nucleic Acids Res. 29, 2502-2509.
16. Zeng, Y., Wagner, E. J. and Cullen, B. R. (2002). Both natural and designed micro RNAs can inhibit the expression of cognate mRNAs when expressed in human cells. Mol. Cell. 9, 1327-1333.
17. Zuker, M. (2003). Mfold web server for nucleic acid folding and hybridization prediction. Nucleic Acids Res. 31, 3406-3415.
18. Hofacker, I. L. (2003). Vienna RNA secondary structure server. Nucleic Acids Res. 13, 3429-3431.

The invention claimed is:

1. A cloning-free and restriction endonuclease-free method to generate a dumbbell-shaped vector that includes an expression cassette comprising:
   i) providing a preparation comprising a single stranded nucleic acid template comprising a target nucleic acid molecule comprising two complementary sequence segments wherein each segment comprises a transcription promoter sequence and further comprises a transcriptional terminator and wherein said two complementary sequence segments are separated by a third sequence segment;
   ii) providing a preparation wherein said single stranded nucleic acid template additionally comprises a stem;
   iii) contacting said single stranded nucleic acid template with a first oligonucleotide primer comprising a 3'-hydroxyl group that is complementary to at least part of the 3' terminal nucleotide sequence of said single stranded nucleic acid template and further comprising a 5' nucleotide sequence not complementary to the target nucleic acid molecule and further contacting said single-stranded nucleic acid with a first set of blocking oligonucleotides comprising one, two, three or more oligonucleotides that are complementary to at least part of the 5' terminal nucleotide sequence of said single stranded nucleic acid template;
   iv) providing polymerase chain reaction components to primer extend the 3' annealed first oligonucleotide primer;
   v) contacting said extended oligonucleotide primer with a second oligonucleotide primer comprising a 3'-hydroxyl group that is complementary to at least part of the 3' terminal nucleotide sequence of said extended oligonucleotide primer and further comprising a 5' nucleotide sequence not complementary to the target nucleic acid molecule and further contacting said single stranded nucleic acid template with a second set of blocking oligonucleotides comprising one, two, three or more oligonucleotides that are complementary to at least part of the 5' terminal nucleotide sequence of said extended oligonucleotide primer;
   vi) polymerase chain amplifying the template to synthesize a pool of extended oligonucleotide primers and annealing said templates to create double stranded nucleic acid comprising a sequence coding for the 3' arm of a hairpin-structured RNA at the 5' nucleotide sequences of the plus strand and the minus strand and comprising a sequence coding for the 5' arm of a hairpin-structured RNA at the 3' nucleotide sequences of the plus strand and the minus strand;
   vii) contacting said pool of extended oligonucleotide primers with a third oligonucleotide primer comprising a 3' hydroxyl group that is complementary to at least part of the 3' terminal nucleotide sequence of the oligonucleotide primer extended by said first oligonucleotide primer and further comprising a 5' nucleotide sequence not complementary to said extended oligonucleotide primer and further contacting said pool of extended oligonucleotide primers with a fourth oligonucleotide primer comprising a 3' hydroxyl group that is complementary to at least part of the 3' terminal nucleotide sequence of the oligonucleotide primer extended by said second oligonucleotide primer and further comprising a 5' nucleotide sequence not complementary to said extended oligonucleotide primer and further contacting said extended oligonucleotide primers with said first and second set of blocking oligonucleotides;

viii) repeating steps iv) and vii) using a fifth and sixth, seventh and eight or more pairs of oligonucleotide primers wherein the last set of primers comprises 3' hydroxyl groups and 5' phosphate groups;

ix) polymerase chain amplifying the template to synthesize a pool of extended oligonucleotide primers and annealing said templates to create double stranded nucleic acid comprising a sequence coding for the 3' arm of a hairpin-structured RNA at the 5' nucleotide sequences of the plus strand and the minus strand and comprising a sequence coding for the 5' arm of a hairpin-structured RNA at the 3' nucleotide sequences of the plus strand and the minus strand;

x) heat denaturing said double stranded nucleic acid and then cooling down to allow intra-molecular refolding of the resulting plus strand and minus strand DNA to create preformed oligomeric stem-loop structures comprised of plus or minus strand DNA;

xi) contacting said preformed oligomeric loops structures of plus strand and minus strand DNA with a single strand-specific DNA ligase to link the terminal 5'-phosphorylated 5' overhang to the terminal 3'-OH group of the 3' overhang of the same DNA strand in an intra-molecular ligation to create covalently closed plus strand-derived and minus strand-derived dumbbell-shaped vector DNA comprising hairpin-structured template DNA for the transcription of hairpin-structured RNA; and xii) contacting said dumbbell-shaped vector DNA with a DNA exonuclease to remove all primers and non-covalently closed DNA that harbours 5' and 3' ends.

2. A cloning-free and restriction endonuclease-free method to generate a dumbbell-shaped dual expression vector comprising two expression cassettes wherein said method comprises:

i) providing a preparation comprising a first single stranded nucleic acid template comprising a target nucleic acid molecule comprising the reverse complement of a first transcriptional promoter at the 5' terminal sequence and the sequence of a second transcriptional terminator at the 3' terminal sequence;

ii) contacting said first single stranded nucleic acid template with a first oligonucleotide primer comprising a 5'-phosphate and a 3'-hydroxyl group that is complementary to at least part of the 3' terminal nucleotide sequence of said single stranded nucleic acid template and further comprising a 5' nucleotide sequence not complementary to the target nucleic acid molecule wherein said oligonucleotide primer comprises a first sequence of interest to be transcribed and further comprising the reverse complement sequence of a first transcriptional terminator and further comprising a modified nucleotide sequence that prevents extension of the 5' nucleotide sequence not complementary to the target nucleic acid molecule;

iii) providing polymerase chain reaction components and primer extending the 3' annealed oligonucleotide primer to form a second template;

iv) contacting said second template with a second oligonucleotide primer comprising a 5'-phosphate and a 3'-hydroxyl group that is complementary to at least part of the 3' terminal nucleotide sequence of said second template and further comprising a 5' nucleotide sequence not complementary to the second template wherein said oligonucleotide primer comprises a second sequence of interest to be transcribed and further comprising the reverse complement sequence of a second transcriptional terminator and further comprising a modified nucleotide sequence that prevents extension of the 5' nucleotide sequence not complementary to the second template;

v) providing polymerase chain reaction components and primer extending the 3' annealed oligonucleotide primer to form a double stranded nucleic acid;

vi) polymerase chain amplifying the double stranded nucleic acid to synthesize a pool of template DNA and annealing said templates to create double stranded nucleic acid comprising a 5' nucleotide sequence not complementary to the target nucleic acid molecule; and vii) contacting the annealed template nucleic acid with a ligase to link the terminal 5'-phosphate of the non-complementary 5' nucleotide sequence to the 3'-OH of said amplified template nucleic acid to create a terminal loop structure.

3. The method according to claim 2, wherein said first oligonucleotide primer comprises a nucleotide sequence that is non-complementary with said target nucleic acid molecule but includes a region of internal complementarity over part of its length that forms a stem loop structure.

4. The method according to claim 2, wherein at least one of said first oligonucleotide primer and said second oligonucleotide primer includes a palindromic nucleotide sequence over part of its length.

5. The method according to claim 2, wherein at least one of said first oligonucleotide primer and said second oligonucleotide primer includes a modification including a site that is not recognised as template for base-pairing during primer extension by the DNA polymerase in said primer.

6. The method according to claim 2, wherein said first oligonucleotide primer includes a modification including an abasic site in said primer.

7. The method according to claim 6, wherein said abasic site is an apurinic/apyrimidinic site.

8. The method according to claim 7, wherein said apurinic/apyrimidinic site comprises a tetrahydrofuran.

9. The method according to claim 6, wherein said abasic site comprises at least one or at least three apurinic/apyrimidinic sites.

10. The method according to claim 6, wherein said abasic site separates the region complementary to the 3' terminal nucleotide sequence of said single stranded nucleic acid template and the 5' nucleotide sequence not complementary to the target nucleic acid molecule.

11. The method according to claim 2, wherein at least one of said first oligonucleotide primer and said second oligonucleotide primer comprises a non-complementary nucleotide sequence comprising a transcriptional terminator.

* * * * *

SEQUENCE LISTING

<160> NUMBER OF SEQ ID NOS: 25

<210> SEQ ID NO 1

```
<211> LENGTH: 133
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 1
agcttcgcgc tcactgagaa gattttctg tgctctcata cagaacttat aagattccca        60
aatccaaaga catttcacgt ttatggtgat ttcccagaac acatagcgac atgcaaatat      120
gaattgtcca gtt                                                         133

<210> SEQ ID NO 2
<211> LENGTH: 125
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 2
ggacaattca tatttgcatg tcgctatgtg ttctgggaaa tcaccataaa cgtgaaatgt        60
ctttggattt gggaatctta taagttctgt atgagagcac agaaaaatct tctcagtgag      120
cgcga                                                                  125

<210> SEQ ID NO 3
<211> LENGTH: 129
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 3
ttctggacaa ttcatatttg catgtcgcta tgtgttctgg gaaatcacca taaacgtgaa        60
atgtctttgg atttgggaat cttataagtt ctgtatgaga gcacagaaaa atcttctcag      120
taggcaaag                                                              129

<210> SEQ ID NO 4
<211> LENGTH: 137
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 4
gatcctttgc ctactgagaa gattttctg tgctctcata cagaacttat aagattccca        60
aatccaaaga catttcacgt ttatggtgat ttcccagaac acatagcgac atgcaaatat      120
gaattgtcca gaaaact                                                     137

<210> SEQ ID NO 5
<211> LENGTH: 43
<212> TYPE: DNA
<213> ORGANISM: Artificial Sequence
<220> FEATURE:
<223> OTHER INFORMATION: Artificial, with partly complementarity to the
      firefly luciferase gene.
```

<400> SEQUENCE: 5
tgaaggctcc tcagaaacag ctccgcgctc actgagaaga ttt         43

<210> SEQ ID NO 6
<211> LENGTH: 46
<212> TYPE: DNA
<213> ORGANISM: Artificial Sequence
<220> FEATURE:
<223> OTHER INFORMATION: Artificial, with partly complementarity to the
      human lamin A/C gene.

<400> SEQUENCE: 6
tgaaagccca gatcgtcacc acccgccgcg ctcactgaga agattt      46

<210> SEQ ID NO 7
<211> LENGTH: 50
<212> TYPE: DNA
<213> ORGANISM: Artificial Sequence
<220> FEATURE:
<223> OTHER INFORMATION: Artificial, with partly complementarity to the
      firefly luciferase gene.

<400> SEQUENCE: 7
agagaggctc ctcagaaaca gctctttgcc tactgagaag attttttctgt    50

<210> SEQ ID NO 8
<211> LENGTH: 52
<212> TYPE: DNA
<213> ORGANISM: Artificial Sequence
<220> FEATURE:
<223> OTHER INFORMATION: Artificial, with partly complementarity to the
      human lamin A/C gene.

<400> SEQUENCE: 8
agagaagccc agatcgtcac caccttttg cctactgaga agattttttct gt    52

<210> SEQ ID NO 9
<211> LENGTH: 125
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 9
ggacaattca tatttgcatg tcgctatgtg ttctgggaaa tcaccataaa cgtgaaatgt    60
ctttggattt gggaatctta taagttctgt atgagagcac agaaaaatct tctcagtgag   120
cgcga                                                                125

<210> SEQ ID NO 10
<211> LENGTH: 129
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 10
ttctggacaa ttcatatttg catgtcgcta tgtgttctgg gaaatcacca taaacgtgaa    60
atgtctttgg atttgggaat cttataagtt ctgtatgaga gcacagaaaa atcttctcag   120
taggcaaag                                                            129

<210> SEQ ID NO 11
<211> LENGTH: 20
<212> TYPE: DNA
<213> ORGANISM: Artificial Sequence
<220> FEATURE:
<223> OTHER INFORMATION: Artificial, with complementarity to the firefly luciferase gene.

<400> SEQUENCE: 11
cgctgggcgt taatcaaaga                    20

<210> SEQ ID NO 12
<211> LENGTH: 18
<212> TYPE: DNA
<213> ORGANISM: Artificial Sequence
<220> FEATURE:
<223> OTHER INFORMATION: Artificial, with complementarity to the human beta actin gene.

<400> SEQUENCE: 12
ctggcaccca gcacaatg                      18

<210> SEQ ID NO 13
<211> LENGTH: 20
<212> TYPE: DNA
<213> ORGANISM: Artificial Sequence
<220> FEATURE:
<223> OTHER INFORMATION: Artificial, with partly complementarity to the firefly luciferase gene.

<400> SEQUENCE: 13
gtgttcgtct tcgtcccagt                    20

<210> SEQ ID NO 14
<211> LENGTH: 20
<212> TYPE: DNA
<213> ORGANISM: Artificial Sequence
<220> FEATURE:
<223> OTHER INFORMATION: Artificial, with complementarity to the human beta actin gene.

<400> SEQUENCE: 14
gccgatccac acggagtact                    20

<210> SEQ ID NO 15
<211> LENGTH: 303
<212> TYPE: DNA
<213> ORGANISM: Artificial Sequence
<220> FEATURE:
<223> OTHER INFORMATION: Artificial, with sequences originating from the promoter of the human H1RNA gene, the human microRNA 30 (hsa-miR-30) precursor, and the firefly luciferase gene.

<400> SEQUENCE: 15
ttttctggac aattcatatt tgcatgtcgc tatgtgttct gggaaatcac cataaacgtg    60
aaatgtcttt ggatttggga atcttataag ttctgtatga gagcacagaa aaatcttctc   120
agtaggcaaa gagctgtttc tgaggagcct ctcttgaagg ctcctcagaa acagctcgcg   180
gctcactgag aagattttc tgtgctctca tacagaactt ataagattcc caaatccaaa   240
gacatttcac gtttatggtg atttcccaga acacatagcg acatgcaaat atgaattgtc   300
cag                                                                303

<210> SEQ ID NO 16
<211> LENGTH: 82

```
<212> TYPE: RNA
<213> ORGANISM: Artificial Sequence
<220> FEATURE:
<223> OTHER INFORMATION: Artificial, with sequences complementary to the
      firefly luciferase gene.

<400> SEQUENCE: 16
cuucucagug agcgcggagc uguuucugag gagccuucaa gagaggcucc ucagaaacag     60
cucuuugccu acugagaaga uu                                             82

<210> SEQ ID NO 17
<211> LENGTH: 303
<212> TYPE: DNA
<213> ORGANISM: Artificial Sequence
<220> FEATURE:
<223> OTHER INFORMATION: Artificial, with sequences originating from the
      promoter of the human H1RNA gene, the human microRNA 30 (hsa-miR-
      30) precursor, and the firefly luciferase gene.

<400> SEQUENCE: 17
ttttctggac aattcatatt tgcatgtcgc tatgtgttct gggaaatcac cataaacgtg     60
aaatgtcttt ggatttggga atcttataag ttctgtatga gagcacagaa aaatcttctc    120
agtgagcgcg gagctgtttc tgaggagcct tcaagagagg ctcctcagaa acagctcttt    180
gcctactgag aagatttttc tgtgctctca tacagaactt ataagattcc caaatccaaa    240
gacatttcac gtttatggtg atttcccaga acacatagcg acatgcaaat atgaattgtc    300
cag                                                                  303

<210> SEQ ID NO 18
<211> LENGTH: 84
<212> TYPE: RNA
<213> ORGANISM: Artificial Sequence
<220> FEATURE:
<223> OTHER INFORMATION: Artificial, with sequences complementary to the
      firefly luciferase gene.

<400> SEQUENCE: 18
cuucucagug aggcaaagag cuguuucuga ggagccucuc uugaaggcuc cucagaaaca     60
gcuccgcgcu cuacugagaa gauu                                           84

<210> SEQ ID NO 19
<211> LENGTH: 303
<212> TYPE: DNA
<213> ORGANISM: Artificial Sequence
<220> FEATURE:
<223> OTHER INFORMATION: Artificial, with sequences originating from the
      promoter of the human H1RNA gene, the human microRNA 30 (hsa-miR-
      30) precursor, and the human lamin A/C gene.

<400> SEQUENCE: 19
ttttctggac aattcatatt tgcatgtcgc tatgtgttct gggaaatcac cataaacgtg     60
aaatgtcttt ggatttggga atcttataag ttctgtatga gagcacagaa aaatcttctc    120
agtaggcaaa agcccagatc gtcaccacct ctcttgaagg tggtgacgat ctgggctcgc    180
gctcactgag aagatttttc tgtgctctca tacagaactt ataagattcc caaatccaaa    240
gacatttcac gtttatggtg atttcccaga acacatagcg acatgcaaat atgaattgtc    300
cag                                                                  303

<210> SEQ ID NO 20
<211> LENGTH: 82
<212> TYPE: RNA
```

<213> ORGANISM: Artificial Sequence
<220> FEATURE:
<223> OTHER INFORMATION: Artificial, with sequences complementary to the
      human lamin A/C gene.

<400> SEQUENCE: 20
cuucucagug agcgcgagcc cagaucguca ccaccuucaa gagagguggu gacgaucugg    60
gcuuuugccu acugagaaga uu                                            82

<210> SEQ ID NO 21
<211> LENGTH: 303
<212> TYPE: DNA
<213> ORGANISM: Artificial Sequence
<220> FEATURE:
<223> OTHER INFORMATION: Artificial, with sequences originating from the
      promoter of the human H1RNA gene, the human microRNA 30 (hsa-miR-
      30) precursor, and the human lamin A/C gene.

<400> SEQUENCE: 21
ttttctggac aattcatatt tgcatgtcgc tatgtgttct gggaaatcac cataaacgtg    60
aaatgtcttt ggatttggga atcttataag ttctgtatga gagcacagaa aaatcttctc   120
agtgagcgcg agcccagatc gtcaccacct caagagagg tggtgacgat ctgggctttt    180
gcctactgag aagattttc tgtgctctca tacagaactt ataagattcc caaatccaaa    240
gacatttcac gtttatggtg atttcccaga acacatagcg acatgcaaat atgaattgtc   300
cag                                                                 303

<210> SEQ ID NO 22
<211> LENGTH: 82
<212> TYPE: RNA
<213> ORGANISM: Artificial Sequence
<220> FEATURE:
<223> OTHER INFORMATION: Artificial, with sequences complementary to the
      human lamin A/C gene.

<400> SEQUENCE: 22
cuucucagug aggcaaaagc ccagaucguc accaccccucu ugaagguggu gacgaucugg   60
gcucgcgcuc acugagaaga uu                                            82

<210> SEQ ID NO 23
<211> LENGTH: 256
<212> TYPE: DNA
<213> ORGANISM: Artificial Sequence
<220> FEATURE:
<223> OTHER INFORMATION: Artificial, with sequences originating from the
      promoter of the human H1RNA gene and the human microRNA 30 (hsa-
      miR-30) precursor.

<400> SEQUENCE: 23
cgcgctcact gagaagattt ttctgtgctc tcatacagaa cttataagat tcccaaatcc    60
aaagacattt cacgtttatg gtgatttccc agaacacata gcgacatgca aatatgaatt   120
gtccagtttt ctggacaatt catatttgca tgtcgctatg tgttctggga aatcaccata   180
aacgtgaaat gtctttggat ttgggaatct tataagttct gtatgagagc acagaaaaat   240
cttctcagta ggcaaa                                                   256

<210> SEQ ID NO 24
<211> LENGTH: 303
<212> TYPE: DNA
<213> ORGANISM: Artificial Sequence
<220> FEATURE:
<223> OTHER INFORMATION: Artificial, with sequences originating from the promoter of the human H1RNA gene, the human microRNA 30 (hsa-miR-
30) precursor, and the firefly luciferase gene.

<400> SEQUENCE: 24

```
tttctggac aattcatatt tgcatgtcgc tatgtgttct gggaaatcac cataaacgtg    60
aaatgtcttt ggatttggga atcttataag ttctgtatga gagcacagaa aaatcttctc   120
agtaggcaaa gagctgtttc tgaggagcct ctcttgaagg ctcctcagaa acagctcgcg   180
gctcactgag aagatttttc tgtgctctca tacagaactt ataagattcc caaatccaaa   240
gacatttcac gtttatggtg atttcccaga acacatagcg acatgcaaat atgaattgtc   300
cag                                                                303
```

<210> SEQ ID NO 25
<211> LENGTH: 303
<212> TYPE: DNA
<213> ORGANISM: Artificial Sequence
<220> FEATURE:
<223> OTHER INFORMATION: Artificial, with sequences originating from the
    promoter of the human H1RNA gene, the human microRNA 30 (hsa-miR-
    30) precursor, and the firefly luciferase gene.

<400> SEQUENCE: 25

```
tttctggac aattcatatt tgcatgtcgc tatgtgttct gggaaatcac cataaacgtg    60
aaatgtcttt ggatttggga atcttataag ttctgtatga gagcacagaa aaatcttctc   120
agtgagcgcg gagctgtttc tgaggagcct tcaagagagg ctcctcagaa acagctcttt   180
gcctactgag aagatttttc tgtgctctca tacagaactt ataagattcc caaatccaaa   240
gacatttcac gtttatggtg atttcccaga acacatagcg acatgcaaat atgaattgtc   300
cag                                                                303
```